US007244878B2

(12) United States Patent
Blumwald et al.

(10) Patent No.: US 7,244,878 B2
(45) Date of Patent: Jul. 17, 2007

(54) INCREASING SALT TOLERANCE IN PLANTS BY OVEREXPRESSION OF VACUOLAR NA$^+$/H$^+$ TRANSPORTERS

(76) Inventors: Eduardo Blumwald, 612 Jerome St., Davis, CA (US) 95616; Maris Apse, 2217 Amar Ct., Davis, CA (US) 95616

(*) Notice: Subject to any disclaimer, the term of this patent is extended or adjusted under 35 U.S.C. 154(b) by 0 days.

(21) Appl. No.: 11/067,558

(22) Filed: Feb. 24, 2005

(65) Prior Publication Data
US 2005/0155105 A1 Jul. 14, 2005

Related U.S. Application Data

(60) Division of application No. 10/155,535, filed on May 24, 2002, now Pat. No. 6,936,750, which is a continuation-in-part of application No. 09/271,584, filed on Mar. 18, 1999, now Pat. No. 7,041,875.

(60) Provisional application No. 60/116,111, filed on Jan. 15, 1999, provisional application No. 60/078,474, filed on Mar. 18, 1998.

(51) Int. Cl.
*A01H 5/00* (2006.01)
*A01H 5/10* (2006.01)
*C12N 15/82* (2006.01)
*C12N 15/29* (2006.01)

(52) U.S. Cl. ............... 800/298; 800/278; 536/23.6; 435/320.1; 435/468; 424/93.2

(58) Field of Classification Search ................ None
See application file for complete search history.

(56) References Cited

U.S. PATENT DOCUMENTS

| | | | |
|---|---|---|---|
| 4,616,100 | A | 10/1986 | McHughen et al. |
| 5,272,085 | A | 12/1993 | Young et al. |
| 5,346,815 | A | 9/1994 | Krulwich et al. |
| 5,411,875 | A | 5/1995 | Hediger |
| 5,563,246 | A | 10/1996 | Krulwich et al. |
| 5,563,324 | A | 10/1996 | Tarczynski et al. |
| 5,639,950 | A | 6/1997 | Verma et al. |
| 5,689,039 | A | 11/1997 | Becker et al. |
| 5,750,848 | A | 5/1998 | Kruger et al. |
| 5,780,709 | A | 7/1998 | Adams et al. |
| 5,859,337 | A | 1/1999 | Gasser et al. |
| 2002/0083487 | A1 | 6/2002 | Fukuda et al. |
| 2003/0046729 | A1 | 3/2003 | Blumwald et al. |
| 2005/0028235 | A1 | 2/2005 | Zhang et al. |
| 2005/0144666 | A1 | 6/2005 | Blumwald et al. |
| 2005/0155105 | A1 | 7/2005 | Blumwald et al. |
| 2005/0204430 | A1 | 9/2005 | Blumwald et al. |

FOREIGN PATENT DOCUMENTS

| | | |
|---|---|---|
| EP | 1143002 A1 | 10/2001 |
| WO | WO 91/06651 | 5/1991 |
| WO | WO 96/39020 | 12/1996 |
| WO | WO 97/13843 | 4/1997 |
| WO | WO 99/47679 | 9/1999 |
| WO | WO 00/37644 | 6/2000 |

OTHER PUBLICATIONS

Yokoi et al, 2002, Plant J. 30:529-539.*
Guo et al, 2004, Proc. Natl. Acad. Sci. USA 101: 9205-9210.*
Yokoi et al, 2002, Plant J. 30:529-529.*
Guo et al, 2004, Proc. Natl. Acad. Sci. USA 101:9205-9210.*
U.S. Appl. No. 10/617,624, filed Jul. 10, 2003, Blumwald.
U.S. Appl. No. 10/620,061, filed Jul. 14, 2003, Blumwald et al.
U.S. Appl. No. 10/944,174, filed Sep. 16, 2004, Fukuda et al.
Apse et al. (2002) "Engineering salt tolerance in plants" Current Opinion in Biotechnology 13: pp. 146-150.
Apse et al. (1999) "Salt tolerance conferred by overexpression of a vauolar Na+/H+ antiport in *Arabidopsis*" Science 285 (5431): pp. 1256-1258.
Apse et al. (1998) "Cloning and Characterization of Plant Sodium/Proton Antiports" 11 International Workshop on Plant Membrane Biology, Aug. 1998, Cambridge, U.K. (Abstract).
Apse et al. (1998) "Identification of putative sodium/proton antiports in *Arabidopsis*" Plant Membrane Biology Workshop Aug. 1998, Cambridge, U.K. (Poster).
Barkla et al. (1995) "Tonoplast Na+/H+ antiport activity and its energization by the vacuolar H+-ATPase in the halophytic plant *Mesembryanthemum crystallinum* L" Plant Physiol. 109: pp. 549-556.
Barkla et al. (1994) "The plant vacuolar Na+/H+ antiport" Symp. Soc. Exp. Biol. 48: pp. 141-153.
Blumwald (2000) "Sodium transport and salt tolerance in plants" Current Opinion in Cell Biology 12: pp. 431-434.
Blumwald et al. (Dec. 1998) "Cloning of plant sodium/proton antiports in *Arabidopsis*" Eastern Regional Meeting of the Canadian Society of Plant Physiologists, Toronto.
Blumwald et al. (Jun. 1998) "Cloning and characterization of a plant sodium/proton antiport" Annual Meeting of the American Society of Plant Physiologists, Madison, USA.
Blumwald et al. (Aug. 1998) "Cloning and characterization of a plant sodium/proton antiports" 11 International Workshop on Plant Membrane Biology, Aug. 1998, Cambridge, U.K.
Blumwald et al. (Aug. 1998) "Cloning and characterization of a plant sodium/proton antiports" Gordon Conference on Drought and Salinity Stress in Plants, Oxford, U.K.
Bohnert et al. (1996) "Strategies for engineering water-stress tolerance in plants" Trends in Biotechnology 14(3): pp. 89-97.
Borgese et al. (1992) "Cloning and expression of a cAMP-activated Na+/H+ exchanger: evidence that the cytoplasmic domain mediates hormonal regulation" PNAS USA 89: pp. 6765-6769.

(Continued)

*Primary Examiner*—Anne Kubelik
(74) *Attorney, Agent, or Firm*—Morrison & Foerster LLP

(57) ABSTRACT

The invention is isolated nucleic acid molecules encoding Na$^+$/H$^+$ exchanger polypeptides for extrusion of monovalent cations from the cytosol of cells to provide the cell with increased salt tolerance. Crop species transformed with the nucleic acid molecule are capable of surviving in soil with high salt levels that would normally inhibit growth of the crop species.

31 Claims, 2 Drawing Sheets

OTHER PUBLICATIONS

Bork (2000) "Powers and Pitfalls in Sequence Analysis: the 70% Hurdle" Genome Research, vol. 10: pp. 398-400.

Bowie et al. (1990) "Deciphering the Message in Protein Sequences: Tolerance to Amino Acid Substitutions" Science, vol. 247, pp. 1306-1310.

Brant et al. (1997) Human Na+/H+ exchanger isoform NHE3 composite cDNA: Genbank Accession No. T51330.

Broun et al. (1998) "Catalytic Plasticity of Fatty Acid Modification Enzymes Underlying Chemical Diversity of Plant Lipids" Science, vol. 282: pp. 1315-1317.

Counillon et al. (May 1993) "A Point Mutation of the Na+/H+ Exchanger Gene (NHE1) and Amplification of the Mutated Allele Confer Amiloride Resistance Upon Chronic Acidosis" Proc. Natl. Acad. Sci. USA 90(10): pp. 4508-4512.

Covitz et al. (Nov. 1997) Expressed sequence tags from a root hair-enriched *Medicago truncatula* cDNA library: GenBank Accession No. AA660573.

Dante et al. (1997) "AC 004655": *Arabidopsis thaliana* BAC TM021B04: EMBL Database Accession No. AC 004655.

Darley et al. (1998) "ANA1 a Na+/H+ Antiporter From *Arabidopsis*?" 11th International Workshop on Plant Membrane Biology, Aug. 1998, Cambridge, U.K.

Dietrich et al. (1997) Sequence of s. cerevisiae lambda 3641 and cosmids 9461, 9831, and 9410: GenBank Accession No. 927695.

Fukuda et al. (Aug. 1999) "AB021878" *Oryza sativa* (Japonica cultivar-group) OsNHX1 mRNA: EMBL Database Accession No. AB021878.

Fukuda et al. (1999) "Molecular Cloning and Expression of the Na+/H+ Exchanger Gene in *Oryza Sativa*"Biochim. Biophys. Acta. 1446 (1-2): pp. 149-155.

Fukuda et al. (1998) "Na+/H+ Antiporter in Tonoplast Vesicles from Rice Roots" Plant Cell Physiol. 39: pp. 196-201.

Fukuda et al. (Mar. 2001) "The Functional analysis of the rice Na+/H+ antiporter gene"Plant Cell Physiol. 42 (Supp.): p. s210.

Gaxiola et al. (1996) "The *Arabidopsis thaliana* proton transporters, AtNhx1 and Avp1, can function in catin detoxification in yeast" PNAS USA 96 (4): pp. 1480-1485.

Gordon-Kamm et al. (1990) "Transformation of Maize Cells and Regneration of Fertile Transgenic Plants" Plant Cell 2: 603-618.

Hahnnenberger et al. (1996) "Functional expression of the *Schizosaccharmyces pombe* Na+/H+ antiporter gene, sod2, in *Saccharomyces cerevisiae*" PMAS USA 93: pp. 5031-5036.

Hiei et al. (1994) "Efficient Transformation of rice mediated by Agrobacterium and sequence analysis of the boundary of the T-DNA" Plant J. 6: pp. 271-282.

Hill et al. (1998) "Functional Analysis of Conserved Histidines in ADP-Glucose Pyrophosporylase from *Escherichia coli*" Biochem. Biophys. Res. Comm. 244: pp. 573-577.

Ichida et al (1996) "Increased Resistance to Extracellular Cation Block by Mutation of the Pore Domain of the *Arabidopsis* Inward-rectifying K+ Channel KAT1" J. Membrane Biol. 151: pp. 53-62.

Jacoby (Aug. 23, 1999) "Botanists design plants with a taste for salt" Chemical Engineering News: p. 9.

Kadyrzhanova et al. (1995) Sequences for STS primer sets: GenBank Accession No. L44032.

Kaufman (Jul. 31, 2001) "A New Strain of Tomatoes, And Don't Hold the Salt" Washington Post: p. A03.

Kinclova et al. (2001) "Functional study of the *Saccharomyces cerevisiae* Nha1p C-terminus" Mol. Microbiol. 40 (3): pp. 656-668.

Lazar et al. (1988) "Transforming Growth Factor a: Mutation of Aspartic Acid 47 and Leucine 48 Results in Different Biological Activities" Molecular and Cellular Biology 8: pp. 1247-1252.

Liu et al. (2000) "Partial Deletion of a Loop Region in the High Affinity K+ Transporter HKT1 Chages Ionic Permeability Leading to Increased Salt Tolerance" J. Biol. Chem. 275 (36): pp. 27924-27932.

Nass and Rao (Aug. 1998) "Novel Localization of a Na+/H+ Exchanger in a late Endosomal Compartment of Yeast" J. Biol. Chem. 273 (33): pp. 21054-21060.

Nass et al. (Oct. 1997) "Intracellular Sequestration of Sodium by a Novel Na+/H+ Exchanger in Yeast Is Enhanced by Mutations in the Plasma Membrane H+—ATPase" J. Biol. Chem. 272 (42): pp. 26145-26152.

Newman et al. (1998) "AC T75860": Arabidopsis cDNA clone of Lambda-PRL2: EMBL Database Accession No. AC T75860.

Numata et al. (Mar. 1998) "Identification of a Mitochondrial Na+/H+ Exchanger" J. Biol. Chem. 273 (12): pp. 6951-6959.

O'Connor (Aug. 2001) "Altered Tomato Thrives in Salty Soil" New York Times.

Ohki et al. (1995) "AC D49589": EMBL Database Accession No. AC D49589.

Ohki et al. (1995) "Preference of recombination sites involved in the formation of extrachromosomal copies of the human alphoid Sau3A repeat family" Nucleic Acids Res. 23L pp. 4986-4991.

Orlowski and Grinstein (Sep. 1997) "Minireview: Na+/H+ Exchangers of Mammalian Cells" J. Biol. Chem. 272 (36): pp. 22373-22376.

PLANTSP (2002) "PlantsP: Functional Genomics of Plant Phosphorylation-PlantsP Protein 27103" Retrieved Feb. 5, 2005, from http://plantsp.sdsc.edu/cgi-bin/detail.cgi?db=plantsp&plants_id=27103.

Rausch et al. (1996) "Salt stress responses of higher plants: The role of proton pumps and Na=/H+ -antiporters" Journal of Plant Physiology 148 (3-4): pp. 425-433.

Rhoads et al. (1998) "Regulation of the cyanide-resistant alternative oxidase of plant mitochondria" J. Biol. Chem. 273 (46): pp. 30750-30756.

Rubio et al. (1999) "Genetic Selection of Mutations in the High Affinity K+ Transporter HKT1 That Define Functions of a Loop Site for Reduced Na+ permeability and Increase Na+ Tolerance" J. Biol. Chem. 274 (11): pp. 6839-6847.

Sasaki et al. (Apr. 1998) Rice cDNA from panicle C91832: GenBank Accession No. C91832.

Sasaki et al. (Apr. 1998) Rice cDNA from panicle C91861: GenBank Accession No. C91861.

Schachtman et al. (1997) "Molecular and functional characeraization of a novel low-affinity cation transporter (LCT1) in higher plants" PNAS USA 94: pp. 11079-11084.

Seki et al. (2002) RAFL6 *Arabidopsis thaliana* cDNA clone: GenBank Accession Nos.: AV785096 and AV798305.

Strathmann et al. (1989) "Diversity of the G-protein family: sequences from five additional alpha subunits in the mouse" Natl. Acad. Sci. USA 86: pp. 7407-7409.

Travis (2001) "Gene Makes Tomatoes Tolerate Salt" Science News 160: p. 68.

Waditee et al. (2001) "Halotolerant Cyanobacterim Aphanothece Halophytica Contains a Na+/H+ Antiporter, Homologous to Eukaryotic Ones, with Novel Ion Specificity Affected by C-terminal Tail" J. Biol. Chem. 276 (40): pp. 36931-36938.

Wood et al. (Nov. 1998) Direct submission schizosaccharomyces pombe chromosome I sequencing project: GenBank Accession No. CAB10103.

Yamamoto et al. (Oct. 1998) Rice cDNA from green shoot: GenBank Accession No. AU032544.

Yokoi et al. (2002) *Arabidopsis thaliana* Na+/H+ exchanger 5 (NHX5) mRNA: GenBank Accession No. AF490589.

Zandonella (Jul. 2001) "Gene modified tomato revels in salty soils"New Scientist. retrieved Feb. 23, 2002, from <http://www.newscientist.com/channel/health/gm-food/dn1092>.

Zhang et al. (2001) "Engineering salt-tolerant *Brassica* plants: Characterization of yeld and seed oil quality in transgenic plants with increased vacuolar sodium accumulation" PNAS USA 98 (22): pp. 12832-18236.

Zhang et al. (2001) "Transgenic salt-tolerant tomato plants accumulate salt in foliage but not in fruit" Nature Biotechnology 19: pp. 765-768.

Al-Karaki, Ghazi N. (2000) "Growth, Water Use Efficiency, and Sodium and Potassium Acquisition by Tomato Cultivars Grown Under Salt Stress." *Journal of Plant Nutrition*, 23(1):1-8.

Cuartero, Jesús et al. (1999) "Tomato and salinity." *Scientia Horticulture*, 78:83-125.

Dierig, D.A. et al. (2001) "Registration of WCL-SL1 Salt Tolerant *Lesquerella fendleri* Germplasm." *Crop. Sci.*, 41:604-605.

Francois, L.E. et al. (1964) "Salt Tolerance of Safflower." *Agronomy Journal*, 58:38-40.

Gisbert, Carmina et al. (May 2000) "The Yeast HAL1 Gene Improves Salt Tolerance of Transgenic Tomato." *Plant Physiology*, 123:393-402.

Mäser, Pascal et al. (Aug. 2001) "Phylogenetic Relationships within Cation Transporter Families of Arabidopsis." *Plant Physiology*, 126:1646-1667.

Nakamura, Tasukazu et al. (1998) "Structural Analysis of *Arabidopsis thaliana* Chromosome 5. VII. Sequence Features of the Regions of 1,013,767 bp Covered by Sixteen Physically assigned P1 and TAC Clones." *DNA Research*, 5:297-308.

Ohta, Masaru et al. (2002) "Introduction of a $Na^+/H^+$ antiporter gene from *Atriplex gmelini* confers salt tolerance to rice." *FEBS Letters*, 26785:1-4.

Rus, A.M. et al. (2001) "Expressing the yeast HAL1 gene in tomato increases fruit yield and enhances $K^+/Na^+$ selectivity under salt stress." *Plant, Cell and Environment*, 24:875-880.

Santa-Maria, Guillermo E. et al. (Dec. 1997) "The HAK1 Gene of Barley Is a Member of a Large Gene Family and Encodes a High-Affinity Potassium Transporter." *The Plant Cell*, 9:2281-2289.

Venema, K. et al. (Jun. 20, 2003) "A Novel Intracellular $K^+/H^+$ Antiporter Related to $Na^+/H^+$ Antiporters Is Important for $K^+$ Ion Homeostasis in Plants." *The Journal of Biological Chemistry*, 278(25):22453-22459.

West, D. W. et al. (1984) "Response of Six Grape Cultivars to the Combined Effects of High Salinity and Rootzone Waterlogging." *J. Amer. Soc. Hort. Sci.*, 109(6):844-851.

Yermanos, D. M. et al (1964) "Soil Salinity Effects on the Chemical Composition of the Oil and the Oil Content of Safflower Seed." *Agronomy Journal*, 54:35-37.

GenBank Accession No. 3850064, Nov. 4, 1998, Source: Fission Yeast; Reference 1 Authors: Murphy L. and Harris, D.; Reference 2 Authors: Wood, V., Barrell, B.G., and Rajandream, M.A.; 2 pgs.

GenBank Accession No. AF106324, Mar. 3, 1999, located at <http://www.ncbi.nlm.nih.gov/entrez/viewer.fcgi?db=nucleotide&val=4324596>, visited on Jan. 26, 2005, 2 pgs.

Chandler et al. (2003) "When negative is positive in functional genomics" *Trends in Plant Science*, 8: 279-285.

Gormat, (Aug. 4, 2001) "Researchers take an element off the table" *Science News*, 160(5): 68.

Nakamura, Yasukazu et al. (Sep. 25, 1998) "Structured Analysis of *Arabidopsis thaliana* Chromosome 5. VII. Sequence Features of the Regions of 1,013,767 bp covered by Sixteen Physically assigned P1 and TAC Clones," *DNA Research*, 5:297-308.

TSE, C.M. et al. (May 5, 1992) "Cloning and Sequencing of a rabbit CDNA encoding an intestinal and kidney-specific Na(+)/H/(+) exchanger isoform (NHE-3)" *J. Biol. Chem.* 267:9340-9346.

Karmazyn et al. (1999) "The Myocardial Na+-H+ Exchange: Structure, Regulation, and Its Role in Heart Disease" *Circ Res.* 85(9):777-786.

Nakamura, Yasukazu et al. (Sep. 25, 1998) "Structured Analysis of *Arabidopsis thaliana* Chromosome 5. VII. Sequence Features of the Regions of 1,013,767 bp covered by Sixteen Physically assigned P1 and TAC Clones," *DNA Research*, 5:297-308.

TSE, C.M. et al. (May 5, 1992) "Cloning and Sequencing of a rabbit CDNA encoding an intestinal and kidney-specific Na(+)/H/(+) exchanger isoform (NHE-3)" *J. Biol. Chem.* 267:9340-9346.

Karmazyn et al. (1999) "The Myocardial Na+-H+ Exchange: Structure, Regulation, and Its Role in Heart Disease" *Circ Res.* 85(9):777-786.

Al-Karaki, Ghazi N. (2000) "Growth, Water Use Efficiency, and Sodium and Potassium Acquisition by Tomato Cultivars Grown Under Salt Stress." *Journal of Plant Nutrition*, 23(1):1-8.

Cuartero, Jesús et al. (1999) "Tomato and salinity." *Scientia Horticulture*, 78:83-125.

Dierig, D.A. et al. (2001) "Registration of WCL-SL1 Salt Tolerant *Lesquerella fendleri* Germplasm." *Crop. Sci.*, 41:604-605.

Francois, L.E. et al. (1964) "Salt Tolerance of Safflower." *Agronomy Journal*, 58:38-40.

Gisbert, Carmina et al. (May 2000) "The Yeast HAL1 Gene Improves Salt Tolerance of Transgenic Tomato." *Plant Physiology*, 123:393-402.

Mäser, Pascal et al. (Aug. 2001) "Phylogenetic Relationships within Cation Transporter Families of *Arabidopsis*." *Plant Physiology*, 126:1646-167.

Nakamura, Tasukazu et al. (1998) "Structural Analysis of *Arabidopsis thaliana* Chromosome 5. VII. Sequence Features of the Regions of 1,013,767 bp Covered by Sixteen Physically assigned P1 and TAC Clones." *DNA Research*, 5:297-308.

Ohta, Masaru et al. (2002) "Introduction of a $Na^+/H^+$ antiporter gene from *Atriplex gmelini* confers salt tolerance to rice." *FEBS Letters*, 26785:1-4.

Rus, A.M. et al. (2001) "Expressing the yeast HAL1 gene in tomato increases fruit yield and enhances $K^+/Na^+$ selectivity under salt stress." *Plant, Cell and Environment*, 24:875-880.

Santa-Maria, Guillermo E. et al. (Dec. 1997) "The HAK 1 Gene of Barley Is a Member of a Large Gene Family and Encodes a High-Affinity Potassium Transporter." *The Plant Cell*, 9:2281-2289.

Venema, K. et al. (Jun. 20, 2003) "A Novel Intracellular $K^+/H^+$ Antiporter Related to $Na^+/H^+$ Antiporters Is Important for $K^+$ Ion Homeostasis in Plants." *The Journal of Biological Chemistry*, 278(25):22453-22459.

West, D. W. et al. (1984) "Response of Six Grape Cultivars to the Combined Effects of High Salinity and Rootzone Waterlogging." *J. Amer. Soc. Hort. Sci.*, 109(6):844-851.

Yermanos, D. M. et al (1964) "Soil Salinity Effects on the Chemical Composition of the Oil and the Oil Content of Safflower Seed." *Agronomy Journal*, 54:35-37.

GenBank Accession No. 3850064, Nov. 4, 1998, Source: Fission Yeast; Reference 1 Authors: Murphy L. and Harris, D.; Reference 2 Authors: Wood, V., Barrell, B.G., and Rajandream, M.A.; 2 pgs.

GenBank Accession No. AF106324, Mar. 3, 1999, located at <http://www.ncbi.nlm.nih.gov/entrez/viewer.fcgi?db=nucleotide&val=4324596>, visited on Jan. 26, 2005, 2 pgs.

* cited by examiner

A. APG-ura⁻ plate containing 0 mM NaCl, pH 5.5.

B. APG-ura⁻ plate containing 200 mM NaCl, pH 5.5

SEQUENCE LISTING

<160> NUMBER OF SEQ ID NOS: 27

<210> SEQ ID NO 1
<211> LENGTH: 2136
<212> TYPE: DNA
<213> ORGANISM: Arabidopsis thaliana

<400> SEQUENCE: 1

| | | | | | | |
|---|---|---|---|---|---|---|
| cggctcctcc | ccgtgcgttt | ctctcaacgc | aactcaatcc | accctgcacg | tgttcctctc | 60 |
| ttttcccgtc | taaatttctc | agtctcgccg | tgaattttgt | tcttctcttg | ttttccgggc | 120 |
| gaatcaaaat | ccgtctcatt | tccaatcgcg | tctccgttgg | tattttacat | gaacgtttag | 180 |
| cggaatctcg | ggtttagctt | cggagctttg | catttgatct | tcgtcgtctg | tgttgtcctc | 240 |
| tctcggattt | tgttttttcg | ccgctgcaaa | tcagagaaat | ctattcctgg | aagtgataag | 300 |
| atcgcttgga | agcgtttcag | attttacacg | tcattggtga | agaaaaaggg | aaaaagaaag | 360 |
| atgacaatgt | tcgcctcttt | aacctctaaa | atgctatcgg | tgtcaacttc | tgatcacgca | 420 |
| tctgtcgttt | cacttaatct | ctttgttgcc | cttctatgtg | cttgtatcgt | cattggccat | 480 |
| cttttggagg | agaatcgatg | gataaacgaa | tccatcactg | ctttattgat | tgggcttggc | 540 |
| actggtgtcg | tcatattgtt | gattagtaga | gggaaaaact | cacatctctt | ggtctttagt | 600 |
| gaagatctct | tctttatata | tcttttgcca | cccataatat | tcaatgcagg | gtttcaagta | 660 |
| aaaaagaagc | agttttttccg | aaattttgta | actattatgg | cttttggcgc | cattgggacc | 720 |
| gtagtttctt | gcaccataat | atctctaggt | gcaattcagt | tctttaagaa | attagacatt | 780 |
| gggacctttg | acttgggcga | ttttcttgca | atcggcgcca | tatttgctgc | aaccgactct | 840 |
| gtatgcacac | tacaggttct | caatcaagat | gagacacctt | tgctttacag | tcttgtattt | 900 |
| ggagagggcg | ttgtgaatga | tgccacatct | gttgtgctct | tcaatgctat | tcagagtttt | 960 |
| gacctcaccc | accttaacca | tgaagcagct | tttcaatttc | ttgggaactt | tttttatctg | 1020 |
| tttctcttga | gcaccggact | tggtgtcgca | actggtctga | taagtgctta | tgtcatcaag | 1080 |
| aaactgtatt | ttggaaggca | ctcgactgat | cgagaagttg | ccctcatgat | gcttatggct | 1140 |
| tatctttcat | atatgcttgc | tgagctattc | gccttgagtg | tatcctaac | tgtattttc | 1200 |
| tgtgggattg | tgatgtccca | ttacacttgg | cacaatgtca | ccgagagctc | aagaattact | 1260 |
| accaagcatg | cctttgctac | tttgtcgttt | ctcgctgaga | cttttatttt | cctctacgtt | 1320 |
| ggaatggatg | cattggacat | agagaaatgg | agattcgtga | gtgacagccc | gggggacatca | 1380 |
| gttgcagtga | gctcaattct | aatgggtcta | gtcatgcttg | gaagagcagc | ttttgtcttt | 1440 |
| cctctttcct | tcttatcaaa | cttagccaag | aagcatcaga | gcgagaaaat | cagcatcaag | 1500 |
| cagcaagttg | tgatctggtg | ggctggtcta | atgagaggtg | ctgtatctat | ggctcttgcc | 1560 |
| tacaataagt | ttacaagatc | agggcacaca | gaattgcgcg | ggaatgcaat | catgattacc | 1620 |
| agtacaataa | ccgtctgtct | ttttagcacc | atggtgtttg | gtatgctaac | caaaccactg | 1680 |
| attagatacc | taatgccaca | ccaaaaagcg | accaccagta | ccacgagtat | gttatcggac | 1740 |
| gatagcactc | cgaaatcaat | ccacattccg | ctcctcgatg | gtgaacagct | agattcattt | 1800 |
| gagttacctg | ggagccacca | ggacgtgcca | cgaccaaaca | gccttcgagg | tttcctcatg | 1860 |
| cgccccacac | ggactgtcca | ctattactgg | agacagtttg | atgatgcctt | catgcgtcct | 1920 |
| gtgtttggtg | gtcgcggatt | cgttcccttt | gtccctggtt | ctccgactga | gagaagcagc | 1980 |
| catgatctta | gtaaaccttg | aggagaaaga | tatatagaaa | cttaaccaaa | aaacttcttc | 2040 | ttgctcttcc ctcttatggt gactagtatt ggtgggggat cctctagagt cgacctgcag  2100 gcatgcaagc ttggagtagt catgtcgtgc tgttca  2136

<210> SEQ ID NO 2
<211> LENGTH: 546
<212> TYPE: PRT
<213> ORGANISM: Arabidopsis thaliana

<400> SEQUENCE: 2

```
Met Thr Met Phe Ala Ser Leu Thr Ser Lys Met Leu Ser Val Ser Thr
 1               5                  10                  15

Ser Asp His Ala Ser Val Val Ser Leu Asn Leu Phe Val Ala Leu Leu
            20                  25                  30

Cys Ala Cys Ile Val Ile Gly His Leu Leu Glu Glu Asn Arg Trp Ile
        35                  40                  45

Asn Glu Ser Ile Thr Ala Leu Leu Ile Gly Leu Gly Thr Gly Val Val
    50                  55                  60

Ile Leu Leu Ile Ser Arg Gly Lys Asn Ser His Leu Leu Val Phe Ser
65                  70                  75                  80

Glu Asp Leu Phe Phe Ile Tyr Leu Leu Pro Pro Ile Ile Phe Asn Ala
                85                  90                  95

Gly Phe Gln Val Lys Lys Lys Gln Phe Phe Arg Asn Phe Val Thr Ile
            100                 105                 110

Met Ala Phe Gly Ala Ile Gly Thr Val Val Ser Cys Thr Ile Ile Ser
        115                 120                 125

Leu Gly Ala Ile Gln Phe Phe Lys Lys Leu Asp Ile Gly Thr Phe Asp
    130                 135                 140

Leu Gly Asp Phe Leu Ala Ile Gly Ala Ile Phe Ala Ala Thr Asp Ser
145                 150                 155                 160

Val Cys Thr Leu Gln Val Leu Asn Gln Asp Glu Thr Pro Leu Leu Tyr
                165                 170                 175

Ser Leu Val Phe Gly Glu Gly Val Val Asn Asp Ala Thr Ser Val Val
            180                 185                 190

Leu Phe Asn Ala Ile Gln Ser Phe Asp Leu Thr His Leu Asn His Glu
        195                 200                 205

Ala Ala Phe Gln Phe Leu Gly Asn Phe Phe Tyr Leu Phe Leu Leu Ser
    210                 215                 220

Thr Gly Leu Gly Val Ala Thr Gly Leu Ile Ser Ala Tyr Val Ile Lys
225                 230                 235                 240

Lys Leu Tyr Phe Gly Arg His Ser Thr Asp Arg Glu Val Ala Leu Met
                245                 250                 255

Met Leu Met Ala Tyr Leu Ser Tyr Met Leu Ala Glu Leu Phe Ala Leu
            260                 265                 270

Ser Gly Ile Leu Thr Val Phe Phe Cys Gly Ile Val Met Ser His Tyr
        275                 280                 285

Thr Trp His Asn Val Thr Glu Ser Ser Arg Ile Thr Thr Lys His Ala
    290                 295                 300

Phe Ala Thr Leu Ser Phe Leu Ala Glu Thr Phe Ile Phe Leu Tyr Val
305                 310                 315                 320

Gly Met Asp Ala Leu Asp Ile Glu Lys Trp Arg Phe Val Ser Asp Ser
                325                 330                 335

Pro Gly Thr Ser Val Ala Val Ser Ser Ile Leu Met Gly Leu Val Met
            340                 345                 350
```

```
Leu Gly Arg Ala Ala Phe Val Phe Pro Leu Ser Phe Leu Ser Asn Leu
        355                 360                 365

Ala Lys Lys His Gln Ser Glu Lys Ile Ser Ile Lys Gln Gln Val Val
    370                 375                 380

Ile Trp Trp Ala Gly Leu Met Arg Gly Ala Val Ser Met Ala Leu Ala
385                 390                 395                 400

Tyr Asn Lys Phe Thr Arg Ser Gly His Thr Glu Leu Arg Gly Asn Ala
                405                 410                 415

Ile Met Ile Thr Ser Thr Ile Thr Val Cys Leu Phe Ser Thr Met Val
            420                 425                 430

Phe Gly Met Leu Thr Lys Pro Leu Ile Arg Tyr Leu Met Pro His Gln
        435                 440                 445

Lys Ala Thr Thr Ser Thr Thr Ser Met Leu Ser Asp Asp Ser Thr Pro
    450                 455                 460

Lys Ser Ile His Ile Pro Leu Leu Asp Gly Glu Gln Leu Asp Ser Phe
465                 470                 475                 480

Glu Leu Pro Gly Ser His Gln Asp Val Pro Arg Pro Asn Ser Leu Arg
                485                 490                 495

Gly Phe Leu Met Arg Pro Thr Arg Thr Val His Tyr Tyr Trp Arg Gln
            500                 505                 510

Phe Asp Asp Ala Phe Met Arg Pro Val Phe Gly Gly Arg Gly Phe Val
        515                 520                 525

Pro Phe Val Pro Gly Ser Pro Thr Glu Arg Ser Ser His Asp Leu Ser
    530                 535                 540

Lys Pro
545

<210> SEQ ID NO 3
<211> LENGTH: 2066
<212> TYPE: DNA
<213> ORGANISM: Arabidopsis thaliana

<400> SEQUENCE: 3
atggtgatcg gattaagcac aatgctggaa aaaacagagg ctcttttcgc ttctgatcat      60
gcatcggtcg tctccatgaa tttgttcgta gctttgcttt gtgcttgcat cgtgcttggt     120
cacttgcttg aggagactcg gtggatgaac gagtcaatca ctgctcttat cattggttcg     180
tgtactggga ttgtgatctt gcttataagt ggaggcaaaa gctcaaggat tcttgtgttt     240
agtgaagatc tcttctttat ttatcttctt ccaccaatta tattcaacgc agggtttcag     300
gttaagaaga agcaattttt tcgcaacttc atgaccatta tgttatttgg tgctattgga     360
actctcattt catttgttat catctcattt ggtgctaaac atcttttcga gaaaatgaat     420
atcggtgatc ttaccattgc ggactatcta gccattggag caatattctc tgctacagac     480 tctgttttgca ccttgcaagt gcttaatcaa gacgagacac ctctcttgta cagtcttgtc     540
tttggagaag gtgtagtgaa cgatgccaca tcggtcgtgc tcttcaatgc aatacagaga     600
ttcgacctca caaatatcaa ttcagccata gctttggagt ttgctggaaa cttttttttac     660 ctctttatct taagcacagc acttggtgtt gcagctggat tgctcagtgc ttttgttatc     720
aagaagctct atataggaag gcactctact gatcgtgaag ttgcacttat gatgctattg     780
gcttacttat catatatgtt ggcagagcta ttccacttga ctctatcttg actgtgttc      840 ttctgcggga ttgttatgtc tcactataca tggcacaatg ttacagataa atccaaggtc     900
actacaaaac atacttttgc tgcaatgtca tttctagctg agattttat cttcctttac      960
```

-continued

```
gttggaatgg acgctctcga tatcgagaaa tgggacgttg tacgcaacag tcctggtcag    1020
tcgattggag ttagttcaat acttcttggg cttattcttc tgggtcgcgc cgcgttcgtg    1080
tttccacttt ccttcttgtc caatttaaca aagtcttcac cggatgagaa aatagactta    1140
aagaaacaag taaccatttg gtgggctggt ctgatgcgtg gtgcagtgtc aatggctctt    1200
gcttataacc agttcacaac ttcaggacac accaaggttc ttgggaacgc atcatgatc     1260 accagtacca tcactgttgt tcttttcagt actgtggtgt ttggattgct aaccaaaccg    1320
ttagtcaaac atttgcagcc ttcatcaaaa cagtcctcca cgaccgcgct gcagatcaca    1380
ctaagatctt ctttccacga tccgatcctc catgagccgt gctcagtac ccaaggccag     1440 tcagaatacg accctgaaca acatgttagc ttcagaatgt tctggaaatc tccgtccagg    1500
gccattcatc attactggag gaaattcgat aacgcagtta tgcgtcgcat atttggtggc    1560
cgaggcgttt caccagtagt tccaggttca cccattgaga atagtgttcc gcaatggagt    1620
gaagaagtag aaaacaagga acaaaacggc gaaccttgat gaccataatg acatgagtaa    1680
gatctttgac ttgttgatcg cgttttttgg cgttgttgga cgcagacgca acatgggccg    1740
gctctaattt tttgcctcca gttttggtat aatggttttg gatgtgagtt cttatttgcc    1800
cggtgtgatt ttttggtttg tggtgtgatt ttgtaaagcc ggtccgtttt tcgttgtttg    1860
agtttgtggt tttgttgaaa aattgtaact gtccatgtaa atagggactg atataggggt    1920
gacttgagta cacctagctc atatgcagac gttagcgtct gcgtttggag attcgagttt    1980
gcgttggtgg gacgtgagca gattttttaa tctaaagttt gtgtacactt tcttgtactt    2040
cttatacaaa acaaagggac acgaat                                          2066
```

<210> SEQ ID NO 4
<211> LENGTH: 552
<212> TYPE: PRT
<213> ORGANISM: Arabidopsis thaliana

<400> SEQUENCE: 4

```
Met Val Ile Gly Leu Ser Thr Met Leu Glu Lys Thr Glu Ala Leu Phe
  1               5                  10                  15

Ala Ser Asp His Ala Ser Val Val Ser Met Asn Leu Phe Val Ala Leu
                 20                  25                  30

Leu Cys Ala Cys Ile Val Leu Gly His Leu Leu Glu Glu Thr Arg Trp
             35                  40                  45

Met Asn Glu Ser Ile Thr Ala Leu Ile Ile Gly Ser Cys Thr Gly Ile
         50                  55                  60

Val Ile Leu Leu Ile Ser Gly Gly Lys Ser Ser Arg Ile Leu Val Phe
 65                  70                  75                  80

Ser Glu Asp Leu Phe Phe Ile Tyr Leu Leu Pro Pro Ile Ile Phe Asn
                 85                  90                  95

Ala Gly Phe Gln Val Lys Lys Lys Gln Phe Phe Arg Asn Phe Met Thr
                100                 105                 110

Ile Met Leu Phe Gly Ala Ile Gly Thr Leu Ile Ser Phe Val Ile Ile
            115                 120                 125

Ser Phe Gly Ala Lys His Leu Phe Glu Lys Met Asn Ile Gly Asp Leu
        130                 135                 140

Thr Ile Ala Asp Tyr Leu Ala Ile Gly Ala Ile Phe Ser Ala Thr Asp
145                 150                 155                 160

Ser Val Cys Thr Leu Gln Val Leu Asn Gln Asp Glu Thr Pro Leu Leu
                165                 170                 175
```

-continued

Tyr Ser Leu Val Phe Gly Glu Gly Val Val Asn Asp Ala Thr Ser Val
            180                 185                 190

Val Leu Phe Asn Ala Ile Gln Arg Phe Asp Leu Thr Asn Ile Asn Ser
            195                 200                 205

Ala Ile Ala Leu Glu Phe Ala Gly Asn Phe Phe Tyr Leu Phe Ile Leu
            210                 215                 220

Ser Thr Ala Leu Gly Val Ala Ala Gly Leu Leu Ser Ala Phe Val Ile
225                 230                 235                 240

Lys Lys Leu Tyr Ile Gly Arg His Ser Thr Asp Arg Glu Val Ala Leu
            245                 250                 255

Met Met Leu Leu Ala Tyr Leu Ser Tyr Met Leu Ala Glu Leu Phe His
            260                 265                 270

Leu Ser Ser Ile Leu Thr Val Phe Phe Cys Gly Ile Val Met Ser His
            275                 280                 285

Tyr Thr Trp His Asn Val Thr Asp Lys Ser Lys Val Thr Thr Lys His
            290                 295                 300

Thr Phe Ala Ala Met Ser Phe Leu Ala Glu Ile Phe Ile Phe Leu Tyr
305                 310                 315                 320

Val Gly Met Asp Ala Leu Asp Ile Glu Lys Trp Asp Val Val Arg Asn
            325                 330                 335

Ser Pro Gly Gln Ser Ile Gly Val Ser Ser Ile Leu Leu Gly Leu Ile
            340                 345                 350

Leu Leu Gly Arg Ala Ala Phe Val Phe Pro Leu Ser Phe Leu Ser Asn
            355                 360                 365

Leu Thr Lys Ser Ser Pro Asp Glu Lys Ile Asp Leu Lys Lys Gln Val
            370                 375                 380

Thr Ile Trp Trp Ala Gly Leu Met Arg Gly Ala Val Ser Met Ala Leu
385                 390                 395                 400

Ala Tyr Asn Gln Phe Thr Thr Ser Gly His Thr Lys Val Leu Gly Asn
            405                 410                 415

Ala Ile Met Ile Thr Ser Thr Ile Thr Val Val Leu Phe Ser Thr Val
            420                 425                 430

Val Phe Gly Leu Leu Thr Lys Pro Leu Val Lys His Leu Gln Pro Ser
            435                 440                 445

Ser Lys Gln Ser Ser Thr Thr Ala Leu Gln Ile Thr Leu Arg Ser Ser
450                 455                 460

Phe His Asp Pro Ile Leu His Glu Pro Leu Leu Ser Thr Gln Gly Gln
465                 470                 475                 480

Ser Glu Tyr Asp Pro Glu Gln His Val Ser Phe Arg Met Phe Trp Lys
            485                 490                 495

Ser Pro Ser Arg Ala Ile His His Tyr Trp Arg Lys Phe Asp Asn Ala
            500                 505                 510

Val Met Arg Arg Ile Phe Gly Gly Arg Gly Val Ser Pro Val Val Pro
            515                 520                 525

Gly Ser Pro Ile Glu Asn Ser Val Pro Gln Trp Ser Glu Glu Val Glu
            530                 535                 540

Asn Lys Glu Gln Asn Gly Glu Pro
545                 550

<210> SEQ ID NO 5
<211> LENGTH: 1800
<212> TYPE: DNA
<213> ORGANISM: Arabidopsis thaliana

<400> SEQUENCE: 5

-continued

```
gctgaatgga ggaagtgatg atttctccgg tggagcacga ccctcagggc caggttaagc    60
agcagcaagc ggccggcgtt ggtatactgc ttcagattat gatgctcgtg ctttccttcg   120
ttctcggcca tgtcctccgc cgtcatcgat ccactatct tcctgaagcc agcggttcgc    180
ttctcattgg tttaatcgtc ggtatacttg ctaatatctc cgacactgag actagcatta   240
ggacgtggtt taatttccac gaagagttct tcttcttgtt tttgttgcct cccatcatat   300
tccagtcagg tttcagtctt caacctaaac cattcttttc taactttgga gccattgtta   360
cctttgctat catcggaact tttgtcgctt cagttgttac tggtggtctg gtttatcttg   420
gcggctctat gtatctcatg tataaacttc cctttgttga gtgtcttatg tttggtgcac   480
ttatatcagc tacggaccct gtcactgtac tctctatatt ccaggatgtg ggcaccgatg   540
ttaacctgta tgctttggtc tttggagaat cagttctgaa tgatgctatg caatatcat   600
tgtacagaac aatgtcctta gtaaaccgcc agtcctcgtc tggggaacat tttttcatgg   660
tggtgatcag gttttttgag acttttgctg gctcaatgtc tgcaggggtt ggggttggat   720
tcacttcagc tttactcttt aagtatgcag gattggacac cgagaatctt cagaacttgg   780
agtgttgtct ctttgtactt ttcccgtatt tttcatacat gcttgcagaa ggtgttggtc   840
tctccggcat tgtttctata ctcttcacag gaattgttat gaagcgctac actttctcaa   900
atctctcaga agcttcacag agtttcgtat cttctttttt tcacttgata tcttcgctag   960
cagaaacttt cacgttcatt tacatgggat tgatattgc catggagcag catagctggt   1020
cccatgttgg gtttatcctt ttctctattt tgtttattgg cgtggctagg gctgtcaatg  1080
tatttgggtg tgcatatttg gtcaacctat ttagacagga gaaccagaag ataccta tga  1140
agcaccaaaa agccctttgg tatagtggac ttcgaggggc aatggcattt gcacttgcac  1200
ttcaatcact tcatgatcta ccagagggtc acggccaaat catctttact gcaaccacaa  1260
ctattgttgt tgtcacggtt ttactaatag gaggttcgac aggtaaaatg ttggaagctt  1320
tggaagttgt aggtgacgat cttgatgact ccatgtctga aggctttgaa gagagcgatc  1380
atcagtatgt ccctcctcct tttagcattg gagcttcatc tgacgaggat acatcatcat  1440
caggaagcag gttcaagatg aagctgaagg agtttcacaa aaccactaca tcattcaccg  1500
cgttggacaa aaactttctg actccgttct tcacaactaa tagtgaggt ggagatggag   1560
atggggagta gcatggaaaa gatgtggatt tgtggtccag gccaagctat aattagagta  1620
cacatatgtc tatgtaagat taacactggt tgattttacc tctcgcaaaa tgcccactat  1680
aaagttgacg atttccaaga catttcgaaa tattatatag atgtatttat tgtggtacat  1740
acaattacca tgtcaataat ctattacaag aagaaactga gcacaaaaaa aaaaaaaaaa  1800
```

<210> SEQ ID NO 6
<211> LENGTH: 521
<212> TYPE: PRT
<213> ORGANISM: Arabidopsis thaliana

<400> SEQUENCE: 6

```
Met Glu Glu Val Met Ile Ser Pro Val Glu His Asp Pro Gln Gly Gln
  1               5                  10                  15

Val Lys Gln Gln Ala Ala Gly Val Gly Ile Leu Gln Ile Met
             20                  25                  30

Met Leu Val Leu Ser Phe Val Leu Gly His Val Leu Arg Arg His Arg
         35                  40                  45

Phe His Tyr Leu Pro Glu Ala Ser Gly Ser Leu Leu Ile Gly Leu Ile
```

```
                      50                  55                  60
Val Gly Ile Leu Ala Asn Ile Ser Asp Thr Glu Thr Ser Ile Arg Thr
 65                  70                  75                  80

Trp Phe Asn Phe His Glu Glu Phe Phe Leu Phe Leu Pro Pro
                     85                  90                  95

Ile Ile Phe Gln Ser Gly Phe Ser Leu Gln Pro Lys Pro Phe Phe Ser
                    100                 105                 110

Asn Phe Gly Ala Ile Val Thr Phe Ala Ile Gly Thr Phe Val Ala
                115                 120                 125

Ser Val Val Thr Gly Gly Leu Val Tyr Leu Gly Gly Ser Met Tyr Leu
                130                 135                 140

Met Tyr Lys Leu Pro Phe Val Glu Cys Leu Met Phe Gly Ala Leu Ile
145                 150                 155                 160

Ser Ala Thr Asp Pro Val Thr Val Leu Ser Ile Phe Gln Asp Val Gly
                165                 170                 175

Thr Asp Val Asn Leu Tyr Ala Leu Val Phe Gly Glu Ser Val Leu Asn
                180                 185                 190

Asp Ala Met Ala Ile Ser Leu Tyr Arg Thr Met Ser Leu Val Asn Arg
                195                 200                 205

Gln Ser Ser Ser Gly Glu His Phe Phe Met Val Val Ile Arg Phe Phe
                210                 215                 220

Glu Thr Phe Ala Gly Ser Met Ser Ala Gly Val Gly Val Gly Phe Thr
225                 230                 235                 240

Ser Ala Leu Leu Phe Lys Tyr Ala Gly Leu Asp Thr Glu Asn Leu Gln
                245                 250                 255

Asn Leu Glu Cys Cys Leu Phe Val Leu Phe Pro Tyr Phe Ser Tyr Met
                260                 265                 270

Leu Ala Glu Gly Val Gly Leu Ser Gly Ile Val Ser Ile Leu Phe Thr
                275                 280                 285

Gly Ile Val Met Lys Arg Tyr Thr Phe Ser Asn Leu Ser Glu Ala Ser
                290                 295                 300

Gln Ser Phe Val Ser Ser Phe His Leu Ile Ser Ser Leu Ala Glu
305                 310                 315                 320

Thr Phe Thr Phe Ile Tyr Met Gly Phe Asp Ile Ala Met Glu Gln His
                325                 330                 335

Ser Trp Ser His Val Gly Phe Ile Leu Phe Ser Ile Leu Phe Ile Gly
                340                 345                 350

Val Ala Arg Ala Val Asn Val Phe Gly Cys Ala Tyr Leu Val Asn Leu
                355                 360                 365

Phe Arg Gln Glu Asn Gln Lys Ile Pro Met Lys His Gln Lys Ala Leu
                370                 375                 380

Trp Tyr Ser Gly Leu Arg Gly Ala Met Ala Phe Ala Leu Ala Leu Gln
385                 390                 395                 400

Ser Leu His Asp Leu Pro Glu Gly His Gly Gln Ile Ile Phe Thr Ala
                405                 410                 415

Thr Thr Thr Ile Val Val Thr Val Leu Leu Ile Gly Gly Ser Thr
                420                 425                 430

Gly Lys Met Leu Glu Ala Leu Glu Val Val Gly Asp Asp Leu Asp Asp
                435                 440                 445

Ser Met Ser Glu Gly Phe Glu Glu Ser Asp His Gln Tyr Val Pro Pro
                450                 455                 460

Pro Phe Ser Ile Gly Ala Ser Ser Asp Glu Asp Thr Ser Ser Ser Gly
465                 470                 475                 480
```

```
Ser Arg Phe Lys Met Lys Leu Lys Glu Phe His Lys Thr Thr Thr Ser
            485                 490                 495

Phe Thr Ala Leu Asp Lys Asn Phe Leu Thr Pro Phe Phe Thr Thr Asn
            500                 505                 510

Ser Gly Gly Gly Asp Gly Asp Gly Glu
            515                 520
```

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide probe

<400> SEQUENCE: 7
ttcttcatat atcttttgcc accc                                         24

<210> SEQ ID NO 8
<211> LENGTH: 28
<212> TYPE: DNA
<213> ORGANISM: Artificial Sequence
<220> FEATURE:
<223> OTHER INFORMATION: PCR Primer

<400> SEQUENCE: 8
ccccaacccc tgcagacatt gagccagc                                     28

<210> SEQ ID NO 9
<211> LENGTH: 33
<212> TYPE: DNA
<213> ORGANISM: Artificial Sequence
<220> FEATURE:
<223> OTHER INFORMATION: PCR Primer

<400> SEQUENCE: 9
gctgaatgga ggaagtgatg atttctccgg tgg                               33

<210> SEQ ID NO 10
<211> LENGTH: 28
<212> TYPE: DNA
<213> ORGANISM: Artificial Sequence
<220> FEATURE:
<223> OTHER INFORMATION: PCR Primer

<400> SEQUENCE: 10
cccgcggatc cggtgcactt atatcagc                                     28

<210> SEQ ID NO 11
<211> LENGTH: 28
<212> TYPE: DNA
<213> ORGANISM: Artificial Sequence
<220> FEATURE:
<223> OTHER INFORMATION: PCR Primer

<400> SEQUENCE: 11
ggcggaattc acaacactcc aagttctg                                     28

<210> SEQ ID NO 12
<211> LENGTH: 35
<212> TYPE: DNA
<213> ORGANISM: Artificial Sequence
<220> FEATURE:
<223> OTHER INFORMATION: PCR Primer

<400> SEQUENCE: 12

```
cgctcccccg ggatggagga agtgatgatt tctcc                              35

<210> SEQ ID NO 13
<211> LENGTH: 33
<212> TYPE: DNA
<213> ORGANISM: Artificial Sequence
<220> FEATURE:
<223> OTHER INFORMATION: PCR Primer

<400> SEQUENCE: 13
ggacgcgtcg acctactccc catctccatc tcc                                33

<210> SEQ ID NO 14
<211> LENGTH: 26
<212> TYPE: DNA
<213> ORGANISM: Artificial Sequence
<220> FEATURE:
<223> OTHER INFORMATION: PCR Primer

<400> SEQUENCE: 14
ggtgaggata ttcagccact tgtctg                                        26

<210> SEQ ID NO 15
<211> LENGTH: 24
<212> TYPE: DNA
<213> ORGANISM: Artificial Sequence
<220> FEATURE:
<223> OTHER INFORMATION: PCR Primer

<400> SEQUENCE: 15
tgtgagatcc cgacccgcaa gatc                                          24

<210> SEQ ID NO 16
<211> LENGTH: 10
<212> TYPE: PRT
<213> ORGANISM: Arabidopsis thaliana

<400> SEQUENCE: 16

Phe Phe Leu Phe Leu Leu Pro Pro Ile Ile
 1               5                  10

<210> SEQ ID NO 17
<211> LENGTH: 24
<212> TYPE: DNA
<213> ORGANISM: Artificial Sequence
<220> FEATURE:
<223> OTHER INFORMATION: PCR Primer

<400> SEQUENCE: 17
ttcgcctctt taacctctaa aatg                                          24

<210> SEQ ID NO 18
<211> LENGTH: 24
<212> TYPE: DNA
<213> ORGANISM: Artificial Sequence
<220> FEATURE:
<223> OTHER INFORMATION: PCR Primer

<400> SEQUENCE: 18
tgtaggcaag agccatagat acag                                          24

<210> SEQ ID NO 19
<211> LENGTH: 28
<212> TYPE: DNA
<213> ORGANISM: Artificial Sequence
```

```
<220> FEATURE:
<223> OTHER INFORMATION: Primer

<400> SEQUENCE: 19
tacagagtcg gttgcagcaa atatggcg                                              28

<210> SEQ ID NO 20
<211> LENGTH: 33
<212> TYPE: DNA
<213> ORGANISM: Artificial Sequence
<220> FEATURE:
<223> OTHER INFORMATION: Primer

<400> SEQUENCE: 20
caccaatact agtcaccata agagggaaga gca                                        33

<210> SEQ ID NO 21
<211> LENGTH: 29
<212> TYPE: DNA
<213> ORGANISM: Artificial Sequence
<220> FEATURE:
<223> OTHER INFORMATION: Primer

<400> SEQUENCE: 21
ctgcctctct ctcaacgcaa ctcaatcca                                             29

<210> SEQ ID NO 22
<211> LENGTH: 26
<212> TYPE: DNA
<213> ORGANISM: Artificial Sequence
<220> FEATURE:
<223> OTHER INFORMATION: PCR Primer

<400> SEQUENCE: 22
gaattcctca acgcaactca atccac                                                26

<210> SEQ ID NO 23
<211> LENGTH: 26
<212> TYPE: DNA
<213> ORGANISM: Artificial Sequence
<220> FEATURE:
<223> OTHER INFORMATION: PCR Primer

<400> SEQUENCE: 23
ctgcagggcg aacattgtca tctttc                                                26

<210> SEQ ID NO 24
<211> LENGTH: 28
<212> TYPE: DNA
<213> ORGANISM: Artificial Sequence
<220> FEATURE:
<223> OTHER INFORMATION: PCR Primer

<400> SEQUENCE: 24
gaattccatt gagaatagtg ttccgcaa                                              28

<210> SEQ ID NO 25
<211> LENGTH: 27
<212> TYPE: DNA
<213> ORGANISM: Artificial Sequence
<220> FEATURE:
<223> OTHER INFORMATION: PCR Primer

<400> SEQUENCE: 25
ctgcaggatt cgtgtccctt tgttttg                                               27
```

```
<210> SEQ ID NO 26
<211> LENGTH: 27
<212> TYPE: DNA
<213> ORGANISM: Artificial Sequence
<220> FEATURE:
<223> OTHER INFORMATION: PCR Primer

<400> SEQUENCE: 26
gaattctcgc ttcagttgtt actggtg                                          27

<210> SEQ ID NO 27
<211> LENGTH: 28
<212> TYPE: DNA
<213> ORGANISM: Artificial Sequence
<220> FEATURE:
<223> OTHER INFORMATION: PCR Primer

<400> SEQUENCE: 27
ctgcagcgct tcataacaat tcctgtca                                         28
```

INCREASING SALT TOLERANCE IN PLANTS BY OVEREXPRESSION OF VACUOLAR $Na^+/H^+$ TRANSPORTERS

CROSS REFERENCE TO RELATED APPLICATIONS

This application is a divisional application of U.S. patent application Ser. No. 10/155,535 filed May 24, 2002, which is a continuation-in-part of U.S. patent application Ser. No. 09/271,584, filed Mar. 18, 1999, which claims priority to U.S. Patent Application Ser. Nos. 60/116,111, filed Jan. 15, 1999, and 60/078,474, filed Mar. 18, 1998, each of which is hereby incorporated in its entirety.

BACKGROUND OF THE INVENTION

Environmental stress due to salinity is one of the most serious factors limiting the productivity of agricultural crops, which are predominantly sensitive to the presence of high concentrations of salts in the soil. Large terrestrial areas of the world are affected by levels of salt inimical to plant growth. It is estimated that 35-45% of the 279 million hectares of land under irrigation is presently affected by salinity. This is exclusive of the regions classified as arid and desert lands, (which comprises 25% of the total land of our planet). Salinity has been an important factor in human history and in the life spans of agricultural systems. Salt impinging on agricultural soils has created instability and has frequently destroyed ancient and recent agrarian societies. The Sumerian culture faded as a power in the ancient world due to salt accumulation in the valleys of the Euphrates and Tigris rivers. Large areas of the Indian subcontinent have been rendered unproductive through salt accumulation and poor irrigation practices. In this century, other areas, including vast regions of Australia, Europe, southwest USA, the Canadian prairies and others have seen considerable declines in crop productivity.

Although there is engineering technology available to combat this problem, though drainage and supply of high quality water, these measures are extremely costly. In most of the cases, due to the increased need for extensive agriculture, neither improved irrigation efficiency nor the installation of drainage systems is applicable. Moreover, in the arid and semi-arid regions of the world water evaporation exceeds precipitation. These soils are inherently high in salt and require vast amounts of irrigation to become productive. Since irrigation water contains dissolved salts and minerals, an application of water is also an application of salt that compounds the salinity problem.

Increasing emphasis is being given to modify plants to fit the restrictive growing conditions imposed by salinity. If economically important crops could be manipulated and made salt resistant, this land could be farmed resulting in greater sales of seed and greater yield of useful crops. Conventional breeding for salt tolerance has been attempted for a long time. These between crop plants and their more salt-tolerant wild relatives (1), b) screening and selecting for variation within a particular phenotype (2), c) designing new phenotypes through recurrent selection (3). The lack of success in generating tolerant varieties (given the low number of varieties released and their limited salt tolerance) (4) would suggest that conventional breeding practices are not enough and that in order to succeed a breeding program should include the engineering of transgenic crops (5).

Several biochemical pathways associated with stress tolerance have been characterized in different plants and a few of the genes involved in these processes have been identified and in some cases the possible role of proteins has been investigated in transgenic/overexpression experiments. Several compatible solutes have been proposed to play a role in osmoregulation under stress. Such compatible solutes, including carbohydrates (6), amino acids (7) and quaternary N-compounds (8) have been shown to increase osmoregulation under stress. Also, proteins that are normally expressed during seed maturation (LEAs, Late Embriogenesis Abundant proteins) have been suggested to play a role in water retention and in the protection of other proteins during stress. The overexpression of LEA in rice provided a moderate benefit to the plants during water stress (9,10). A single gene (sod2) coding for a $Na^+/H^+$ antiport has been shown to confer sodium tolerance in fission yeast (11,12), although the role of this plasma membrane-bound protein appears to be only limited to yeast. One of the main disadvantages of using this gene for transformation of plants is associated with the typical problems encountered in heterologous gene expression, i.e. incorrect folding of the gene product, targeting of the protein to the target membrane and regulation of the protein function.

Plants that tolerate and grow in saline environments have high intracellular salt levels. A major component of the osmotic adjustment in these cells is accomplished by ion uptake. The utilization of inorganic ions for osmotic adjustment suggests that salt-tolerant plants must be able to tolerate high levels of salts within their cells. However, enzymes extracted from these plants show high sensitivity to salt. The sensitivity of the cytosolic enzymes to salt would suggest that the maintenance of low cytosolic sodium concentration, either by compartmentation in cell organelles or by exclusion through the plasma membrane, must be necessary if the enzymes in the cell are to be protected from the inimical effects of salt.

Plant cells are structurally well suited to the compartmentation of ions. Large membrane-bound vacuoles are the site for a considerable amount of sequestration of ions and other osmotically active substances. A comparison of ion distribution in cells and tissues of various plant species indicates that a primary characteristic of salt tolerant plants is their ability to exclude sodium out of the cell and to take up sodium and to sequester it in the cell vacuoles. Transport mechanisms could actively move ions into the vacuole, removing the potentially harmful ions from the cytosol. These ions, in turn, could act as an osmoticum within the vacuole, which would then be responsible for maintaining water flow into the cell. Thus, at the cellular level both specific transport systems for sodium accumulation in the vacuole and sodium extrusion out of the cell are correlated with salt tolerance.

SUMMARY OF THE INVENTION

We have isolated the first such system of intracellular salt management. We identified the presence of a functional vacuolar $Na^+/H^+$ antiport in the vacuolar membrane of higher plants (13, 14, 15, 16, 17, 18).

We have demonstrated the $Na^+/H^+$ antiport function in isolated tonoplast membranes and in intact vesicles and we showed that the activity of antiport molecules was salt dependent. Neither a protein sequence nor a gene encoding the antiport were identified in previously published work. We have now identified nucleic acid molecules coding for plant $Na^+/H^+$ antiports, the nucleic acid molecules and polypeptides produced by the nucleic acid molecules being the subject of the present invention. These polypeptides are useful for the extrusion of sodium ions from the cytosol, either through the accumulation of sodium ions into the vacuoles or into the extracellular space, thus providing the most important trait for salt tolerance in plants. These nucleic acid molecules, preferably genes, are useful for the engineering of salt tolerant plants by transformation of salt-sensitive crops overexpressing one or more of these nucleic acid molecules under the control of constitutively active promoters or under the control of conditionally-induced promoters. Agrobacterium tumefaciens-mediated transformation or particle-bombardment-mediated transformation are useful for depending upon the plant species.

The invention-includes an isolated nucleic acid molecule encoding a PNHX transporter polypeptide, or a fragment of a polypeptide having $Na^+/H^+$ transporter activity and capable of increasing salt tolerance in a cell. In particular, the present invention is directed to plant $Na^+/H^+$ transporters having the nucleotide sequences depicted in SEQ ID NO: 1, 3 and 5. The present invention is further directed to plant $Na^+/H^+$ transporters having the protein sequences depicted in SEQ ID NO: 2, 4 and 6. The present invention is futher directed to plant $Na^+/H^+$ transporters having nucleotide sequences encoding the protein sequences depicted in SEQ ID NO: 2, 4 and 6. The present invention is futher directed to transgenic plants expressing recombinant DNA sequences encoding the protein sequences depicted in SEQ ID NO: 2, 4 and 6.

The invention also relates to an isolated nucleic acid molecule encoding a THX transporter polypeptide, PNHX transporter polypeptide, or a fragment of a polypeptide having $Na^+/H^+$ transporter activity and capable of increasing salt tolerance in a cell, comprising a nucleic acid molecule selected from the group consisting of:
  (a) a nucleic acid molecule that hybridizes to all or part of a nucleic molecule of SEQ ID NOS: 1, 3, and/or 5, or a complement thereof under moderate or high stringency hybridization conditions, wherein the nucleic acid molecule encodes a TNHX transporter polypeptide, a PNHX transporter polypeptide or a polypeptide having $Na^+/H^+$ transporter activity and capable of increasing salt tolerance in a cell;
  (b) a nucleic acid molecule degenerate with respect to (a), wherein the nucleic molecule encodes a TNHX transporter polypeptide, a PNHX transporter polypeptide or a polypeptide having $Na^+/H^+$ transporter activity and capable of increasing salt tolerance in a cell.

The hybridization conditions preferably comprise moderate (also called intermediate) or high stringency conditions selected from the conditions in Table 4.

The invention also includes an isolated nucleic acid molecule encoding a THX transporter polypeptide or a PNHX transporter polypeptide, or a fragment of a polypeptide having $Na^+/H^+$ transporter activity and capable of increasing salt tolerances in a cell, comprising a nucleic acid molecule selected from the group consisting of:
  (a) the nucleic acid molecule of the coding strand shown in SEQ ID NO: 1, SEQ ID NO:3, SEQ ID NO:5, or a complement thereof;
  (b) a nucleic acid molecule encoding the same amino acid sequence as a nucleotide sequence of (a); and
  (c) a nucleic acid molecule having at least 17% identity with the nucleotide sequence of (a) and which encodes a THX transporter polypeptide or the PNHX transporter polypeptide or a polypeptide having $Na^+/H^+$ transporter activity.

The THX transporter polypeptide or the PNHX transporter polypeptide preferably comprises an AtNHX transporter polypeptide. An AtNHX transporter polypeptide is a polypeptide isolated from *Arabidopsis thaliana* having $Na^+/H^+$ transporter activity and capable of increasing salt tolerance in a cell. The nucleic acid molecule may comprise all or part of a nucleotide sequence in SEQ ID NO:1, SEQ ID NO:3, SEQ ID NO:5 (or the coding region thereof).

The invention also includes an AtNHX nucleic acid molecule isolated from *Arabidopsis thaliana*, or a fragment thereof encoding a transporter polypeptide having $Na^+/H^+$ transporter activity and capable of increasing salt tolerance in a cell.

Another aspect of the invention relates to a recombinant nucleic acid molecule comprising a nucleic acid molecule and a constitutive promoter sequence or an inducible promoter sequence, operatively linked so that the promoter enhances transcription of the nucleic acid molecule in a host cell.

The nucleic acid molecule preferably comprises genomic DNA, cDNA or RNA. In another aspect, the nucleic acid molecule is chemically synthesized. The nucleic acid molecule is preferably isolated from *Arabidopsis thaliana*.

The nucleic acid molecule preferably encodes a TNHX transporter polypeptide or PNHX transporter polypeptide that is capable of extruding monovalent cations out of the cytosol of a cell to provide the cell with increased salt tolerance, wherein the monovalent cations are selected from at least one of the group consisting of sodium, lithium and potassium. The cell preferably comprises a plant cell. The monovalent cations are preferably extruded into a vacuole or into the extracellular space.

The invention also includes an isolated nucleic acid molecule comprising a nucleic acid molecule selected from the group consisting of 8 to 10 nucleotides of the nucleic acid molecules described above, 11 to 25 nucleotides of the nucleic acid molecules described above, and 26 to 50 nucleotides of the nucleic acid molecules described above.

Another aspect of the invention relates to a vector comprising a nucleic acid molecule of the invention. The vector preferably comprises a promoter selected from the group consisting of a super promoter, a 35S promoter of cauliflower mosaic virus, a drought-inducible promoter, an ABA-inducible promoter, a heat shock-inducible promoter, a salt-inducible promoter, a copper-inducible promoter, a steroid-inducible promoter and a tissue-specific promoter.

The invention also includes a host cell comprising a recombinant nucleic acid molecule of the invention, or progeny of the host cell.

The host cell is preferably selected from the group consisting of a fungal cell, a yeast cell, a bacterial cell, a microorganism cell and a plant cell. The plant, a plant part, a seed, a plant cell or progeny thereof preferably comprises the recombinant nucleic acid molecule of the invention. The plant part preferably comprises all or part of a leaf, a flower, a stem, a root or a tuber. The plant, plant part, seed or plant cell is preferably of a species selected from the group consisting of potato, tomato, brassica, cotton, sunflower, strawberries, spinach, lettuce, rice, soybean, corn, wheat, rye, barley, atriplex, sorgum, alfalfa, salicornia and the plant species or types in the specification.

The plant, plant part, seed or plant cell preferably comprises a dicot plant or a monocot plant.

The invention also relates to a method for producing a recombinant host cell capable of expressing the nucleic acid molecule of the invention, the method comprising introducing into the host cell a vector of the invention. The invention also includes a method of producing a genetically transformed plant which expresses TNHX or PNHX transporter polypeptide, comprising regenerating a genetically transformed plant from a plant cell, seed or plant part of the invention. In one method, the genome of the host cell also includes a functional TNHX or PNHX gene. In another method, the genome of the host cell does not include a functional TNHX or PNHX gene. The invention also includes a transgenic plant produced according to a method of the invention.

Another aspect of the invention relates to a method for expressing a TNHX or PNHX transporter polypeptide in the host cell of the invention, a the plant, plant part, seed or plant cell of the invention, the method comprising culturing the host cell under conditions suitable for gene expression. A method for producing a transgenic plant that expresses elevated levels of PNHX transporter polypeptide relative to a non-transgenic plant, comprising transforming a plant with the vector of the invention. The invention also relates to an isolated polypeptide encoded by and/or produced from a nucleic acid molecule of the invention, or the vector of the invention.

The invention also relates to an isolated PNHX transporter polypeptide or a fragment thereof having $Na^+/H^+$ transporter activity and capable of increasing salt tolerance in a cell. The polypeptide of the invention preferably comprises an AtNHX transporter polypeptide. The polypeptide of the invention preferably comprises all or part of an amino acid sequence in SEQ ID NOS: 2, 4 or 6. The invention also includes a polypeptide fragment of the AtNHX transporter polypeptide of the invention, or a peptide mimetic of the AtNHX transporter polypeptide, having $Na^+/H^+$ transporter activity and capable of increasing salt tolerance in a cell. The polypeptide fragment of the invention preferably consists of at least 20 amino acids, having $Na^+/H^+$ transporter activity and capable of increasing salt tolerance in a cell. The fragment or peptide mimetic of the invention is preferably capable of being bound by an antibody to a polypeptide of the invention. In one embodiment, the polypeptide of the invention is recombinantly produced.

The invention also includes an isolated and purified transporter polypeptide comprising the amino acid sequence of a TNHX transporter polypeptide or a PNHX transporter polypeptide, wherein the transporter polypeptide is encoded by a nucleic acid molecule that hybridizes under moderate or stringent conditions to a nucleic acid molecule of SEQ ID NOS: 1, 3 or 5, a degenerate form thereof or a complement. The invention also includes a polypeptide comprising a sequence having greater than 28% sequence identity to a polypeptide of the invention (preferably a polypeptide such as SEQ ID NOS: 2, 4 or 6).

The polypeptide of the invention, preferably comprises a $Na^+/H^+$ transporter polypeptide. The polypeptide is preferably isolated from *Arabidopsis thaliana*.

The invention also includes an isolated nucleic acid molecule encoding polypeptide of the invention (preferably SEQ ID NOS: 2, 4, or 6).

Another aspect of the invention relates to an antibody directed against a polypeptide of the invention. The antibody of the invention, preferably comprises a monoclonal antibody or a polyclonal antibody.

The invention relates to a method of producing a genetically transformed plant which expresses or overexpresses a TNHX transporter polypeptide, a PNHX transporter polypeptide or a polypeptide having $Na^+/H^+$ transporter activity and capable of increasing salt tolerance in a cell and wherein the plant has increased salt tolerance, comprising:
 a) cloning or synthesizing a TNHX nucleic acid molecule, a PNHX nucleic acid molecule or a nucleic acid molecule which codes for a $Na^+/H^+$ transporter polypeptide, wherein the polypeptide is capable of providing salt tolerance to a plant;
 b) inserting the nucleic acid molecule in a vector so that the nucleic acid molecule is operably linked to a promoter;
 c) inserting the vector into a plant cell or plant seed;
 d) regenerating the plant from the plant cell or plant seed, wherein salt tolerance in the plant is increased compared to a wild type plant.

The invention includes a transgenic plant produced according to a method of the invention.

The nucleic acid molecules have several uses which will be discussed in more detail below. The nucleic acid molecules and the polypeptides are used in a method for protecting a plant from the adverse affects of a saline environment by incorporating a nucleic acid molecule for salt tolerance and/or the polypeptide of the invention into a plant. The nucleic acid molecules of the invention are also useful for the identification of homologous nucleic acid molecules from plant species, preferably salt tolerant species and genetically engineering salt tolerant plants of agricultural and commercial interest.

The invention relates to isolated necleic acid molecules encoding a polypeptide for extrusion of sodium ions from the cytosol of a cell to provide the cell with salt tolerance. The nucleic acid molecules preferably comprise the nucleotide sequence of SEQ ID NOS: 1, 3, and/or 5. The nucleic acid molecules may be DNA or RNA. The nucleic acid molecules may be used to transform a cell selected from the group consisting of a planet cell, a yeast cell and a bacterial cell. The sodium ions are extruded into a vacuole or out of the cell. The nucleic acid molecules encode a $Na^+/H^+$ exchanger polypeptide.

In a preferred embodiment, the nucleic acid molecules are isolated from *Arabidopsis thaliana*.

The invention includes an isolated nucleic acid molecule, comprising SEQ ID NOS: 1, 3, and/or 5. The invention also relates to an isolated nucleic acid molecule, comprising a sequence having greater than 17% homology to the sequences of the invention described in the preceding paragraphs.

In an alternate embodiment, the nucleic acid molecule consists of a sequence selected from the group consisting of 8 to 10 nucleotides of the nucleic acid molecules of the invention, 11 to 25 nucleotides of the nucleic acid molecule and 26 to 50 nucleotides of the nucleic acid molecules. These nucleic acid molecules hybridize to nucleic acid molecules described in the preceding paragraphs.

The nucleic acid molecule of the invention may have a sense or an antisense sequence.

In an alternate embodiment, the invention is an expression vector comprising a nucleic acid molecule of the invention. The expression vector preferably consists of a promoter selected from the group consisting of a super promoter, a 35S promoter of cauliflower mosaic virus, a drought-inducible promoter, an ABA-inducible promoter, a heat shock-inducible promoter, a salt-inducible promoter, a copper-inducible promoter, a steroid inducible promoter and a tissue-specific promoter.

The invention is a polypeptide produced from the nucleic acid molecules of the invention. The invention is also a polypeptide produced from the expression vector. The polypeptide is used for extrusion of sodium ions from the cytosol of a cell to provide the cell with salt tolerance.

In a preferred embodiment, the polypeptide has the amino acid sequence of SEQ ID NOS: 2, 4, and/or 6. The polypeptides may be homologous to the polypeptide of SEQ ID NOS: 2, 4, and/or 6. In an alternate embodiment, the polypeptides comprise a sequence having greater than 28% hololgy to the polypeptide of SEQ ID NOS: 2, 4, or 6. The polypeptides are Na$^+$/H$^+$ exchanger polypeptides.

The polypeptides are preferably isolated from *Arabidopsis thaliana*.

The invention also includes a monoclonal antibody or polyclonal antibody directed against a polypeptide of the invention.

Another embodiment of the invention includes a transformed microorganism comprising an isolated nucleic acid molecule of the invention. The invention also includes a transformed microorganism including an expression vector.

The invention includes a plant cell transformed with a nucleic acid molecule of the invention. The invention also includes a yeast cell transformed with the nucleic acid molecule of the invention. In another embodiment, the invention is a plant, plant part or seed, generated from a plant cell transformed with a nucleic acid molecule of the invention. The invention also relates to a plant, plant part, seed or plant cell transfected with a nucleic acid molecule of the invention. The plant, plant part, seed or plant cell is preferably selected from a species selected from the group consisting of potato, tomato, brassica, cotton, sunflower, strawberries, spinach, lettuce, rice, soybean, corn, wheat, rye, barley, atriplex, sorgum, alfalfa and salicornia and other plants described herein.

The invention also includes a method for producing a polypeptide of the invention by culturing a plant, plant part, seed or plant cell of the invention and recovering the expressed polypeptide from the culture.

The invention includes an isolated nucleic acid molecule encoding a polypeptide capable of extruding monovalent cations from the cytosol of a cell to provide the cell with increased salt tolerance. The nucleic acid molecule preferably includes the nucleotide sequences of SEQ ID NOS: 1, 3, and/or 5. The nucleic acid molecule is preferably DNA or RNA. The cell is preferably a plant cell, a yeast cell or a bacterial cell. The monovalent cations are preferably sodium, lithium or potassium. The monovalent cations are preferably extruded into a vacuole or out of the cell. The nucleic acid molecules preferably encode a Na$^+$/H$^+$ exchanger polypeptide. The nucleic acid molecule is preferably isolated from *Arabidopsis thaliana*.

The invention also includes an isolated nucleic acid molecule, including a sequence having greater than 17% homology to a sequence referred to in the preceding paragraph.

The invention also includes a nucleic acid molecule of 8 to 10 nucleotides, 11 to 25 or 26 to 50 nucleotides of a nucleic acid molecule of the invention.

The invention also includes a nucleic acid molecule which nucleic acid molecule hybridizes a nucleic acid molecule of the invention. The nucleic acid molecule comprises a sense or an antisense sequence.

The invention also includes an expression vector including a nucleic acid molecule of the invention. The expression vector preferably comprises a promoter selected from the group consisting of a super promoter, a 35S promoter of cauliflower mosaic virus, a drought-inducible promoter, an ABA-inducible promoter, a heat shock-inducible promoter, a salt-inducible promoter, a copper-inducible promoter, a steroid-inducible promoter and a tissue-specific promoter.

The invention also includes a polypeptide produced from a nucleic acid molecule or expression vector of the invention. The invention also includes a polypeptide for extrusion of monovalent cations ions from the cytosol of a cell to provide the cell with salt tolerance. The invention also includes a polypeptide including the amino acid sequence of SEQ ID NOS: 2, 4, and/or 6 or a polypeptide homologous to one of these sequences. The invention also includes a polypeptide including a sequence having greater than 28% homology to one of these polypeptides. The polypeptide is preferably a Na$^+$/H$^+$ exchanger polypeptide isolated from *Arabidopsis thaliana*. The invention also includes a peptide including at least 5 amino acids or 41 to 75 amino acids of the polypeptide of the invention. The invention also includes nucleic acid molecules these polypeptides.

The invention includes a polypeptide for extrusion of monovalent cations ions from the cytosol of a cell to provide the cell with salt tolerance, including, but not necessarily having, an amiloride binding domain.

Another aspect of the invention relates to a monoclonal or polyclonal antibody directed against a polypeptide of the invention.

Another variation includes a transformed microorganism including an isolated nucleic acid molecule of the invention. The transformed microorganism preferably includes an expression vector of the invention.

A plant cell, yeast cell transformed or transfected with a nucleic acid molecule or a plant, plant part or seed, generated from the plant cell. The plant, plant part, seed or plant cell is preferably from a species selected from the group consisting of Alfalfa, Almond, Apple, Apricot, Arabidopsis, Artichoke, Atriplex, Avocado, Barley, Beet, Birch, Brassica, Cabbage, Cacao, Cantaloup/cantalope, Carnations, Castorbean, Cauliflower, Celery, Clover, Coffee, Corn, Cotton, Cucumber, Garlic, Grape, Grapefruit, Hemp, Hops, Lettuce, Maple, Melon, Mustard, Oak, Oat, Olive, Onion, Orange, Pea, Peach, Pear, Pepper, Pine, Plum, Poplar, Potato, Prune, Radish, Rape, Rice, Roses, Rye, Sorghum, Soybean, Spinach, Squash, Strawberries, Sunflower, Sweet corn, Tobacco, Tomato and Wheat. The invention also includes a method for producing a peptide, by culturing the plant, plant part, seed or plant cell and recovering the expressed peptide from the culture.

The invention includes a nucleic acid molecule that encodes all or part of a polypeptide capable of extruding monovalent cations from the cytosol of a cell to provide the cell with salt tolerance, wherein the sequence hybridizes to the nucleic acid molecule of all or part of SEQ ID NO: 1 or SEQ ID NO:3, SEQ ID NO:5 under low, medium and high stringency conditions.

The invention includes an isolated nucleic acid molecule encoding a polypeptide capable of extruding monovalent cations from the cytosol of a cell to provide the cell with salt tolerance, including at least one of the nucleic acid molecules of SEQ ID NOS: 1, 3, and/or 5. The molecule is preferably DNA or RNA. The cell is preferably selected from the group consisting of a plant cell, a yeast cell and a bacterial cell and encodes a Na$^+$/H$^+$ exchanger polypeptide isolated from *Arabidopsis thaliana*.

It will be clear to one skilled in the art that SEQ ID NOS: 1, 3, and/or 5 are useful as probes, for example, in isolating other salt tolerant nucleic acid molecules or in preparing transgenic plants and performing many of the other methods of the invention that are described with respect to SEQ ID NOS: 1, 2, 3, 4, 5, and/or 6. Variants and modifications of FIG. 1 sequences are also included within the invention as are methods using varied or modified sequences (the same preferred percentages of identity and sequence described with respect to SEQ ID NOS: 1, 2, 3, 4, 5, and 6.)

BRIEF DESCRIPTION OF THE DRAWINGS

Preferred embodiments of the invention are described in relation to the drawings in which:

FIG. 1A Shows 60 µg of tonoplast samples from Δnhx1+AtNHX5 yeast line (lane1) and Δnhx1+pYpGE15 vector line (lane2) blocked with anti X5-GST fusion protein antibody, displaying a 57 KDa band for the full ORF transformants.

FIG. 1B Shows 60 µg of tonoplast samples from Δnhx1+AtNHX5-S yeast line (lane1) and Δnhx1+pYpGE15 vector line (lane2) blocked with anti X5-GST fusion protein antibody, displaying a 40 KDa band for the short ORF transformants.

FIG. 2A shows different yeast transformants on 0 mM NaCl. From top to bottom: WT yeast transformed with empty pYpGE15 vector (WT+pYpGE15); Δnhx1 transformed with empty pYpGE15 vector (Δhx1+pYpGE15); Δnhx1 transformed with AtNHX5-pYpGE15 construct (Δnhx1+AtNHX5-pYpGE15); and Δnhx1 transformed with the short version of AtNHX3 cloned in pYpGE15 vector (Δnhx1+AtNHX5-S-pYpGE15).

FIG. 2B shows different yeast transformants on 200 mM NaCl. From top to bottom: WT yeast transformed with empty pYpGE15 vector (WT+pYpGE15); Δnhx1 transformed with empty pYpGE15 vector (Δhx1+pYpGE15); Δnhx1 transformed with AtNHX5-pYpGE15 construct (Δnhx1+AtNHX5-pYpGE15); and Δnhx1transformed with the short version of AtNHX3 cloned in pYpGE15 vector (Δnhx1+AtNHX5-S-pYpGE15).

DETAILED DESCRIPTION OF THE INVENTION

Figure 1:
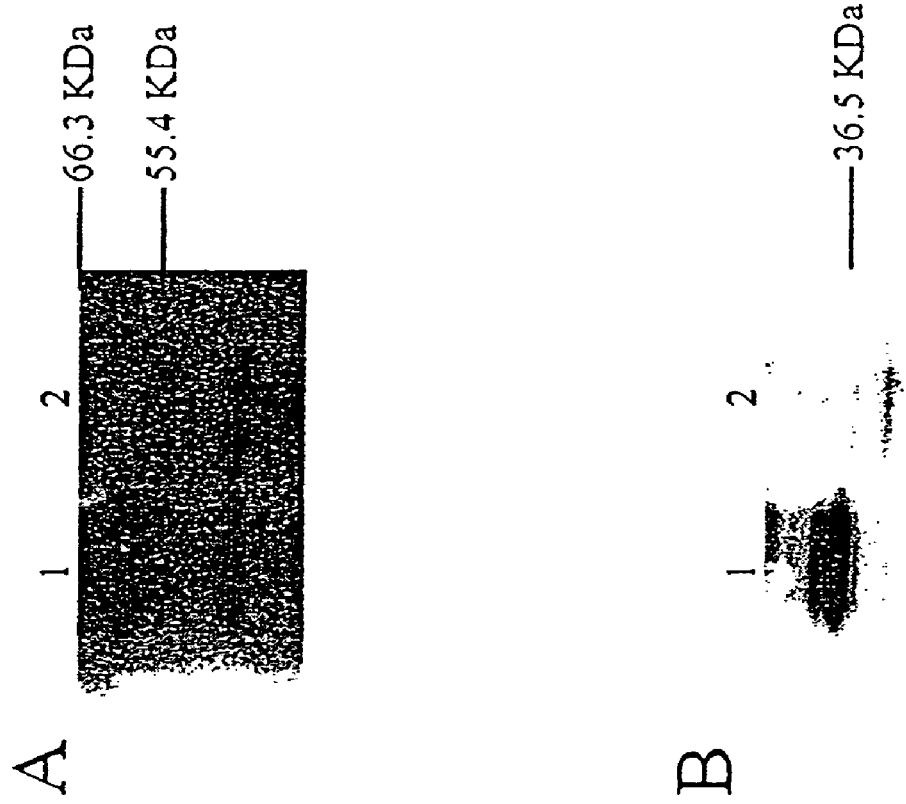
FIG. 1 shows Western-blotting used to detect the expression in yeast of both the full and short length of AtNHX5.

Salt Tolerance Nucleic Acid Molecules and Polypeptides

The invention relates to nucleic acid molecules and polypeptides which increase salt tolerance in cells and plants. PNHX polypeptides are plant $Na^+/H^+$ transporter polypeptides that are capable of increasing and enhancing salt tolerance in a cell, preferably a plant cell. These transporters (also referred to as exchangers, antiports or antiporters) extrude monovalent cations (preferably potassium ions or lithium ions, most preferably sodium ions) out of the cytosol. The cations are preferably extruded into the vacuoles or extracellular space. The affinity for particular ions varies between transporters. The listed preferences refer to the cations that are most likely to be abundant in the cytosol and therefore most likely to be extruded. It is not necessarily a reflection of transporter affinity for particular cations. The PNHX nucleic acid molecules which encode PNHX polypeptides are particularly useful in producing transgenic plants which have increased salt tolerance compared to a wild type plant.

It will also be apparent that there are polypeptide and nucleic acid molecules from other organisms, such as yeast, microorganisms, fish, birds or mammals, that are similar to PNHX polypeptides and nucleic acid molecules. The entire group of $Na^+/H^+$ transporter polypeptides and nucleic acid molecules that are capable of increasing salt tolerance in a cell (including PNHX and AtNHX polypeptides and nucleic acid molecules) are collectively referred to as ("TNHX polypeptides" and "TNHX nucleic acid molecules"). TNHX polypeptides are $Na^+/H^+$ transporters that are capable of increasing salt tolerance in a cell, preferably a plant cell, because they extrude monovalent cations (preferably potassium ions or lithium ions, most preferably sodium ions) out of the cytosol.

The role of TNHX and PNHX nucleic acid molecules and polypeptides in maintaining salt tolerance was not shown before this invention. The ability of these compounds to increase salt tolerance of transgenic host cells (particularly plant cells) and transgenic plants compared to wild type cells and plants was unknown.

PNHX and TNHX polypeptides need not necessarily have the primary function of providing salt tolerance. All nucleotides and polypeptides which are suitable for use in the methods of the invention, such as the preparation of transgenic host cells or transgenic plants, are included within the scope of the invention. Genomic clones or cDNA clones are preferred for preparation of transgenic cells and plants.

In a preferred embodiment, the invention relates to cDNAs encoding $Na^+/H^+$ exchangers from *Arabidopsis thaliana*. The cDNA sequences and the corresponding amino acid sequences for AtNHX2, AtNHX4, and AtNHX5 are presented as SEQ ID NOS: 2, 4, and 6.

Function of Salt Tolerance Nucleic Acid Molecules

The polypeptides of the invention allow the extrusion of monovalent cations (preferably potassium ions or lithium ions, most preferably sodium ions) from the cytosol, which in this application preferably refers to the transport and accumulation of sodium ions into the vacuoles or into the extracellular space (outside of the cell), thus providing the most important trait for salt tolerance in plants. Antiport polypeptides from organisms other than plants have shown different specificity for monovalent ions (e.g. D. G. Warnock, A. S. Pollock, "Sodium Proton Exchange in Epithelial Cells", pages 77-90, in S. Grinstein ed. Sodium Proton Exchange, (1987, CRC Press, USA).) TNHX and PNHX transporters will also show different specificity between transporters. The nucleic acid molecules of the invention allow the engineering of salt tolerant plants by transformation of crops with this nucleic acid molecule under the control of constitutively active promoters or under the control of conditionally-inducible promoters. The resulting expression or overexpression of these nucleic acid molecules confers increased salt tolerance in plants grown in soil, solid, semi-solid medium or hydroponically.

The PNHX Nucleic Acid Molecule and Polypeptide is Conserved in Plants

Sequence Identity

This is the first isolation of a nucleic acid molecule encoding a $Na^+/H^+$ exchanger from plant species. It is widely known amongst those skilled in the art that *Arabidopsis thaliana* is a model plant for many plant species. Nucleic acid sequences having sequence identity to the AtNHX sequences are found in other plants, in particular halophytes such as *Beta Vulgaris* and Atriplex. Sequences from *Arabidopsis thaliana* and other plants are collectively referred to as "PNHX" nucleic acid sequences and polypeptides. We isolate PNHX nucleic acid molecules from plants having nucleic acid molecules that are similar to those in *Arabidopsis thaliana*, such as beet, tomato, rice, cucumber, radish and other plants as in Table 5 and using techniques described in this application. The invention includes methods of isolating these nucleic acid molecules and polypeptides as well as methods of using these nucleic acid molecules and polypeptides according to the methods described in this application, for example those used with respect to AtNEX.

Table 1 below shows several sequences with sequence identity and sequence similarity to the AtNHX polypeptides. Where polypeptides are shown, a suitable corresponding DNA encoding the polypeptide will be apparent. These sequences code for polypeptides similar to portions of AtNHX polypeptides. The sequences in Table 2 are useful to make probes to identity full length sequences or fragments (from the listed species or other species). One skilled in the art would be able to design a probe based on a polypeptide or peptide fragment. The invention includes nucleic acid molecules of about: 10 to 50 nucleotides, 50 to 200 nucleotides, 200 to 500 nucleotides, 500 to 1000 nucleotides, 1000 to 1500 nucleotides, 1500 to 1700 nucleotides, 1700 to 2000 nucleotides, 2000 to 2500 nucleotides or at least 2500 nucleotides and which include all or part of the sequences (or corresponding nucleic acid molecule) in Table 2. The invention also includes peptides and polypeptides of about: 10 to 50 amino acids, 50 to 200 amino acids, 200 to 500 amino acids, 500 to 750 amino acids or at least 750 amino acids which encode all or part of the polypeptides in Table 2 (wherein the polypeptide is produced according to a reading frame aligned with an AtNHX polypeptide). Possible modifications to these sequences will also be apparent. The polypeptide and nucleic acid molecules are also useful in research experiments or in bioinformatics to locate other sequences. The nucleic acid molecules and polypeptides preferably provide $Na^+/H^+$ transporter activity and are capable of moving monovalent cations from the cytosol of the cell into vacuoles or the extracellular space (in this application, extracellular space refers to the space outside a cell in an organism or the space outside a cultured cell).

TABLE 1

| Organism | GenBank Accession No. |
| --- | --- |
| Yeast (*S. pombe*) | 3850064 |
| Yeast (*Saccharomyces cervisae*) | 927695 |
| Rice EST | C 91832 |
| Rice EST | C 91861 |
| Rice EST | AV032544 |
| *Medicago Trunculata* EST | AA660573 |
| *Hordeum Vulgare* STS | L 44032 |

As shown in Table 2 below, many nucleic acid molecules identified in *Arabidopsis thaliana* have striking DNA sequence similarity to nucleic acid molecules encoding the homologous polypeptide in other plant species. Using the techniques described in this application and others known in the art, it will be apparent that the nucleic acid molecule encoding the homologous $Na^+/H^+$ exchanger in other plant species including, but not limited to plants of agricultural and commercial interest, will have DNA sequence identity (homology) at least about >17%, >20%, >25%, >35% to SEQ ID NOS: 1, 3, and/or 5 (or a partial sequence thereof). Some plants species may have DNA with a sequence identity (homology) at least about: >50%, >60%, >70%, >80% or >90% more preferably at least about >95%, >99% or >99.5%, to SEQ ID NOS: 1, 3, or 5 (or a partial sequence thereof). The invention also includes modified nucleic acid molecules from plants other than *Arabidopsis thaliana* which have sequence identity at least about: >17%, >20%, >25%, >35%, >50%, >60%, >70% >80% or >90% more preferably at least about >95%, >99% or >99.5%, to an AtNHX sequence of SEQ ID NOS: 1, 3, and/or 5 (or a partial sequence thereof). Modified nucleic acid molecules are discussed below. Preferably about 1, 2, 3, 4, 5, 6 to 10, 10 to 25, 26 to 50 or 51 to 100, or 101 to 250 nucleotides or amino acids are modified. Sequence identity is most preferably calculated as the number of identical amino acid residues expressed as a percentage of the length of the shorter of the two sequences in a pairwise alignment. The pairwise alignment is constructed preferably using the Clustal W program preferably using the following parameter settings: fixed gap penalty=10, floating gap penalty=10, protein weight matrix=BLOSUM62.

The invention also includes nucleic acid molecules encoding polypeptides having sequence similarity taking into account conservative amino acid substitutions. Sequence similarity (and preferred percentages) are discussed below.

It will be apparent that nucleic acid molecule encoding the homologous $Na^+/H^+$ exchanger in other species (preferably plants) including, but not limited to plants of agricultural and commercial interest, will hybridize to all or part of SEQ ID NOS: 1, 3, and/or 5 (or a partial sequence thereof) under low, moderate (also called intermediate conditions) or high stringency conditions. Preferred hybridization conditions are described below.

The invention includes the nucleic acid molecules from other plants as well as methods of obtaining the nucleic acid molecules by, for example, screening a cDNA library or other DNA collection with a probe of the invention (such as a probe comprising at least about: 10 or preferably at least 15 or 30 nucleotides of AtNHX2, AtNHX4 or AtNHX5 and detecting the presence of a TNHX or PNHX nucleic acid molecule). Another method involves comparing the AtNHX sequences e.g. SEQ ID NOS: 1, 3, or 5 to other sequences, for example using bioinformatics techniques such as database searches or alignment strategies, and detecting the presence of a TNHX or PNHX nucleic acid molecule or polypeptide. The invention includes the nucleic acid molecule and/or polypeptide obtained according to the methods of the invention. The invention also includes methods of using the nucleic acid molecules, for example to make probes, in research experiments or to transform host cells or make transgenic plants. These methods are as described below.

The polypeptides encoded by the homologous TNHX or PNHX nucleic acid molecules in other species will have amino acid sequence identity. The preferred percentage of sequence identity for sequences of the invention includes sequences having identity of at least about: 30% to AtNHX1, 31% to AtNHX2, 36% to AtNHX3, and 36% to AtNHX4. Sequence identity may be at least about: >20%, >25%, >28%, >30%, >35%, >40%, >50% to SEQ ID NOS: 2, 4, and/or 6 (or a partial sequence thereof). Some polypeptides may have a sequence identity of at least about: >60%, >70%, >80% or >90%, more preferably at least about: >95%, >99% or >99.5% to SEQ ID NOS: 2, 4, and/or 6 (or a partial sequence thereof). Identity is calculated according to methods known in the art. Sequence identity is most preferably assessed by the Clustal W program. The invention also includes modified polypeptides from plants which have sequence identity at least about: >20%, >25%, >28%, >30%, >35%, >40%, >50%, >60%, >70%, >80% or >90% more preferably at least about >95%, >99% or >99.5%, to an AtNHX sequence of SEQ ID NOS: 2, 4, or 6 (or a partial sequence thereof). Modified polypeptides molecules are discussed below. Preferably about: 1, 2, 3,4, 5, 6 to 10, 10 to 25, 26 to 50 or 51 to 100, or 101 to 250 nucleotides or amino acids are modified.

TABLE 2

|  | Polypeptide | DNA |
|---|---|---|
| Plant Vacuolar H⁺-PPiase (vacuolar pyrophosphatase) | | |
| *Arabidopsis* (Accession # 282878) | 100% | 100% |
| Beet (Accession # 485742) | 88.7% | 72.8% |
| Tobacco (Accession # 1076627) | 89.9% | 68.4% |
| Rice (Accession # 1747296) | 85% | 70.4% |
| Tonoplast Intrinsic Polypeptide (water channel) | | |
| *Arabidopsis* (Accession # X63551) | 100% | 100% |
| *Curcubita* (Cucumber) (Accession # D45078) | 66.5% | 39.1% |
| *Raphanus* (radish) (Accession # D84669) | 56.7% | 37.4% |
| *Helianthus* (Accession # X95951) | 50.4% | 35.2% |
| High Affinity Ammonium Transporter | | |
| *Arabidopsis* (Accession # X75879) | 100% | 100% |
| Tomato (Accession # X95098) | 73.5% | 62.9% |
| Rice (Accession # AF001505) | 66.6% | 58.1% |

Nucleic Acid Molecules and Polypeptides Similar to AtNHX

Those skilled in the art will recognize that the nucleic acid molecule sequences in FIGS. 1(*a*), (*b*) and (*c*) are not the only sequences which may be used to provide increased salt tolerance in plants. The genetic code is degenerate so other nucleic acid molecules which encode a polypeptide identical to an amino acid sequence in FIG. 1(*a*), (*b*) or (*c*) may also be used. The sequence of the other nucleic acid molecules of this invention may also be varied without changing the polypeptide encoded by the sequence. Consequently, the nucleic acid molecule constructs described below and in the accompanying examples for the preferred nucleic acid molecules, vectors, and transformants of the invention are merely illustrative and are not intended to limit the scope of the invention.

Those skilled in the art will recognize that the nucleic acid molecule sequences of SEQ ID NOS: 1, 3, and/or 5 are not the only sequences which may be used to provide increased salt tolerance in plants. The genetic code is degenerate so other nucleic acid molecules which encode a polypeptide identical to an amino acid sequence of SEQ ID NOS: 2, 4, and/or 6 may also be used. The sequence of the other nucleic acid molecules of this invention may also be varied without changing the polypeptide encoded by the sequence. Consequently, the nucleic aced molecule constructs described below and in the accompanying examples for the preferred nucleic, vectors, and transformants of the invention are merely illustrative and are not intended to limit the scope of the invention.

Sequence Identity

The invention includes modified nucleic acid molecules with a sequence identity at least about: >17%, >20%, >30%, >40%, >50%, >60%, >70%, >80% or >90% more preferably at least about >95%, >99% or >99.5%, to a DNA sequence of SEQ ID NOS: 1, 3, and/or 5 (or a partial sequence thereof). Preferably about 1, 2, 3, 4, 5, 6 to 10, 10 to 25, 26 to 50 or 51 to 100, or 101 to 250 nucleotides or amino acids are modified. Identity is calculated according to methods known in the art. Sequence identity is most preferably assessed by the Clustal W program. For example, if a nucleotide sequence (called "Sequence A") has 90% identity to a portion of the nucleotide sequence in SEQ ID NO: 1, then Sequence A will be identical to the referenced portion of the nucleotide sequence in SEQ ID NO: 1, except that Sequence A may include up to 10 point mutations, such as deletions or substitutions with other nucleotides, per each 100 nucleotide of the referenced portion of SEQ ID NO: 1. Nucleotide sequences functionally equivalent to the PNHX or AtNHX sequences can occur in a variety of forms as described below. Polypeptides having sequence identity may be similarly identified.

The polypeptides encoded by the homologous NHX, PHX Na⁺/H⁺ exchange nucleic acid molecule in other species will have amino acid sequence identity (also known as homology) at least about: >20%, >25%, >28%, >30%, >40% or >50% to an amino acid sequence of SEQ ID NOS: 2, 4, and/or 6 (or a partial sequence thereof). Some plants species may have polypeptides with a sequence identity (homology) of at least about: >60%, >70%, >80% or >90%, more preferably at least about: >95%, >99% or >99.5% to all or part of an amino acid sequence of SEQ ID NOS: 2, 4, and/or 6 (or a partial sequence thereof). Identity is calculated according to methods known in the art. Sequence identity is most preferably assessed by the Clustal W program. Preferably about: 1, 2, 3, 4, 5, 6 to 10, 10 to 25, 26 to 50 or 51 to 100, or 101 to 250 nucleotides or amino acids are modified.

The invention includes nucleic acid molecules with mutations that cause an amino acid change in a portion of the polypeptide not involved in providing salt tolerance and ion transport or an amino acid change in a portion of the polypeptide involved in providing salt tolerance so that the mutation increases or decreases the activity of the polypeptide.

Hybridization

Other functional equivalent forms of the AtNHX nucleic acid molecules encoding nucleic acids can be isolated using conventional DNA-DNA or DNA-RNA hybridization techniques. These nucleic acid molecules and the AtNHX sequences can be modified without significantly affecting their activity.

The present invention also includes nucleic acid molecules that hybridize to one or more of the of SEQ ID NOS: 1, 3, and/or 5 (or a partial sequence thereof) or their complementary sequences, and that encode expression for peptides or polypeptides exhibiting substantially equivalent activity as that of an AtNHX polypeptide produced by the DNA of SEQ ID NOS: 1, 3, and/or 5 or their variants. Such nucleic acid molecules preferably hybridize to the sequences under low, moderate (intermediate), or high stringency conditions. (see Sambrook et al. (Most recent edition) Molecular Cloning: A Laboratory Manual, Cold Spring Harbor Laboratory Press, Cold Spring Harbor, N.Y.).

The present invention also includes nucleic acid molecules from any source, whether modified or not, that hybridize to genomic DNA, cDNA, or synthetic DNA molecules that encode the amino acid sequence of an AtNHX polypeptide, or genetically degenerate forms, under salt and temperature conditions equivalent to those described in this application, and that code for a peptide, polypeptide or polypeptide that has Na⁺/H⁺ transporter activity. Preferably the polypeptide has the same or similar activity as that of an AtNHX polypeptide. The nucleic acid molecules may encode TNHX or PNHX polypeptides. A nucleic acid molecule described above is considered to be functionally equivalent to an AtNHX nucleic acid molecule (and thereby having Na⁺/H⁺ transporter activity) of the present invention if the polypeptide produced by the nucleic acid molecule displays the following characteristics: the polypeptide mediates the proton-dependent sodium transport and sodium-dependent proton transport in intact cells, isolated organelles and purified membrane vesicles. These sodium/proton movements should be higher (preferably at least about 50% higher and most preferably at least about 100% higher) than the proton movements observed in the presence of a background of potassium ions and/or other monovalent cations (i.e. rubidium, cesium, etc., but most preferably not lithium) (13,14).

The invention also includes nucleic acid molecules and polypeptides having sequence similarity taking into account conservative amino acid substitutions. Sequence similarity (and preferred percentages) are discussed below.

Modifications to Nucleic Acid Molecule or Polypeptide Sequence

Changes in the nucleotide sequence which result in production of a chemically equivalent or chemically similar amino acid sequences are included within the scope of the invention. Variants of the polypeptides of the invention may occur naturally, for example, by mutation, or may be made, for example, with polypeptide engineering techniques such as site directed mutagenesis, which are well known in the art for substitution of amino acids. For example, a hydrophobic residue, such as glycine can be substituted for another hydrophobic residue such as alanine. An alanine residue may be substituted with a more hydrophobic residue such as leucine, valine or isoleucine. A negatively charged amino acid such as aspartic acid may be substituted for glutamic acid. A positively charged amino acid such as lysine may be substituted for another positively charged amino acid such as arginine.

Therefore, the invention includes polypeptides having conservative changes or substitutions in amino acid sequences. Conservative substitutions insert one or more amino acids which have similar chemical properties as the replaced amino acids. The invention includes sequences where conservative substitutions are made that do not destroy Na$^+$/H$^+$ transporter activity of the transporter polypeptide. Sequence similarity is preferably calculated as the number of similar amino acids in a pairwise alignment expressed as a percentage of the shorter of the two sequences in the alignment. The pairwise alignment is preferably constructed using the Clustal W program, using the following parameter settings: fixed gap penalty=10, floating gap penalty=10, protein weight matrix=BLOSUM62. Similar amino acids in a pairwise alignment are those pairs of amino acids which have positive alignment scores defined in the preferred protein weight matrix (BLOSUM62). The protein weight matrix BLOSUM62 is considered appropriate for the comparisons described here by those skilled in the art of bioinformatics. (The reference for the Clustal W program (algorithm) is Thompson, J. D., Higgins, D: G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680; and the reference for BLOSUM62 scoring matrix is Henikoff, S. and Henikoff, J. G. (1993) Performance evaluation of amino acid substitution matrices. Proteins, 7:49-61.)

Polypeptides comprising one or more d-amino acids are contemplated within the invention. Also contemplated are polypeptides where one or more amino acids are acetylated at the N-terminus. Those of skill in the art recognize that a variety of techniques are available for constructing polypeptide mimetics with the same or similar desired biological activity (Na$^+$/H$^+$ transporter activity) as the corresponding polypeptide compound of the invention but with more favorable activity than the polypeptide with respect to solubility, stability, and/or susceptibility to hydrolysis and proteolysis. See, for example, Morgan and Gainor, *Ann. Rep. Med. Chem.*, 24:243-252 (1989). Examples of polypeptide mimetics are described in U.S. Pat. No. 5,643,873. Other patents describing how to make and use mimetics include, for example in, U.S. Pat. Nos. 5,786,322, 5,767,075, 5,763,571, 5,753,226, 5,683,983, 5,677,280, 5,672,584, 5,668,110, 5,654,276, 5,643,873. Mimetics of the polypeptides of the invention may also be made according to other techniques known in the art. For example, by treating a polypeptide of the invention with an agent that chemically alters a side group by converting a hydrogen group to another group such as a hydroxy or amino group. Mimetics preferably include sequences that are either entirely made of amino acids or sequences that are hybrids including amino acids and modified amino acids or other organic molecules.

The invention also includes hybrid nucleic acid molecules and polypeptides, for example where a nucleotide sequence from one species of plant is combined with a nucleotide sequence from another sequence of plant, mammal or yeast to produce a fusion polypeptide. The invention includes a fusion protein having at least two components, wherein a first component of the fusion protein comprises a polypeptide of the invention, preferably a full length AtNHX polypeptide. The second component of the fusion protein preferably comprises a tag, for example GST, an epitope tag or an enzyme. The fusion protein may comprise lacZ.

The invention also includes polypeptide fragments of the polypeptides of the invention which may be used to confer salt tolerance if the fragments retain Na$^+$/H$^+$ transporter activity. The invention also includes polypeptides fragments of the polypeptides of the invention which may be used as a research tool to characterize the polypeptide or its activity. Such polypeptides preferably consist of at least 5 amino acids. In preferred embodiments, they may consist of 6 to 10, 11 to 15, 16 to 25, 26 to 50, 51 to 75, 76 to 100 or 101 to 250 amino acids of the polypeptides of the invention (or longer amino acid sequences). The fragments preferably have sodium/proton transporter activity. Fragments may include sequences with one or more amino acids removed, for example, C-terminus amino acids in an AtNHX sequence.

The invention also includes a composition comprising all or part of an isolated TNHX or PNHX (preferably AtNHX) nucleic acid molecule of the invention and a carrier, preferably in a composition for plant transformation. The invention also includes a composition comprising an isolated TNHX or PNHX polypeptide (preferably AtNHX) and a carrier, preferably for studying polypeptide activity.

Recombinant Nucleic Acid Molecules

The invention also includes recombinant nucleic acid molecules comprising a nucleic acid molecule of the invention and a promoter sequence, operatively linked so that the promoter enhances transcription of the nucleic acid molecule in a host cell (the nucleic acid molecules of the invention may be used in an isolated native gene or a chimeric gene (for example, where a nucleic acid molecule coding region is connected to one or more heterologous sequences to form a gene). The promoter sequence is preferably a constitutive promoter sequence or an inducible promoter sequence, operatively linked so that the promoter enhances transcription of the DNA molecule in a host cell. The promoter may be of a type not naturally associated with the cell. Transcription is enhanced with promoters known in the art such as the "Super-promoter" (20) or the 35S promoter of cauliflower mosaic virus (21).

Inducible promoters are also used. These include:
a) drought- and ABA-inducible promoters which may include ABA-responsive elements (22,23)
b) heat shock-inducible promoters which may contain HSEs (heat shock elements) as well as CCAAT box sequences (24)
e) salt-inducible promoters which may include AT and PR elements (25)
d) Copper-inducible promoter that includes ACE1 binding sites (26)
e) steroid-inducible promoter that includes the glucocorticoid response element along with an expression vector coding for a mammalian steroid receptor (27).

In addition, tissue specific expression is achieved with the use of tissue-specific promoters such as, the Fd (Ferredoxin) promoter that mediates high levels of expression in green leaves (28) and peroxidase promoter for root-specific expression (29). These promoters vary in their transcription initiation rate and/or efficiency.

A recombinant nucleic acid molecule for conferring salt tolerance may also contain suitable transcriptional or translational regulatory elements. Suitable regulatory elements may be derived from a variety of sources, and they may be readily selected by one with ordinary skill in the art. Examples of regulatory elements include: a transcriptional promoter and enhancer or RNA polymerase binding sequence, a ribosomal binding sequence, including a translation initiation signal. Additionally, depending on the vector employed, other genetic elements, such as selectable markers, may be incorporated into the recombinant molecule. Markers facilitate the selection of a transformed host cell. Such markers include genes associated with temperature sensitivity, drug resistance, or enzymes associated with phenotypic characteristics of the host organisms.

Nucleic acid molecule expression levels are controlled with a transcription initiation region that regulates transcription of the nucleic acid molecule or nucleic acid molecule fragment of interest in a plant, bacterial or yeast cell. The transcription initiation region may be part of the construct or the expression vector. The transcription initiation domain or promoter includes an RNA polymerase binding site and an mRNA initiation site. Other regulatory regions that may be used include an enhancer domain and a termination region. The regulatory elements described above may be from animal, plant, yeast, bacterial, fungal, viral or other sources, including synthetically produced elements and mutated elements.

Methods of modifying DNA and polypeptides, preparing recombinant nucleic acid molecules and vectors, transformation of cells, expression of polypeptides are known in the art. For guidance, one may consult the following U.S. Pat. Nos. 5,840,537, 5,850,025, 5,858,719, 5,710,018, 5,792,851, 5,851,788, 5,759,788, 5,840,530, 5,789,202, 5,871,983, 5,821,096, 5,876,991, 5,422,108, 5,612,191, 5,804,693, 5,847,258, 5,880,328, 5,767,369, 5,756,684, 5,750,652, 5,824,864, 5,763,211, 5,767,375, or U.S. Pat. No. 5,750,848. Many of these patents also provide guidance with respect to experimental assays, probes and antibodies, transformation of host cells and regeneration of plants, which are described below. These patents, like all other patents, publications (such as articles and Genbank publications) in this application, are incorporated by reference in their entirety.

Host Cells Including a Salt Tolerance Nucleic Acid Molecule

In a preferred embodiment of the invention, a plant or yeast cell is transformed with a nucleic acid molecule of the invention or a fragment of a nucleic acid molecule and inserted in a vector.

Another embodiment of the invention relates to a method of transforming a host cell with a nucleic acid molecule of the invention or a fragment of a nucleic acid molecule, inserted in a vector. The invention also includes a vector comprising a nucleic acid molecule of the invention. The TNHX, PNHX and AtNHX nucleic acid molecules can be cloned into a variety of vectors by means that are well known in the art. The recombinant nucleic acid molecule may be inserted at a site in the vector created by restriction enzymes. A number of suitable vectors may be used, including cosmids, plasmids, bacteriophage, baculoviruses and viruses. Suitable vectors are capable of reproducing themselves and transforming a host cell. The invention also relates to a method of expressing polypeptides in the host cells. A nucleic acid molecule of the invention may be used to transform virtually any type of plant, including both monocots and dicots. The expression host may be any cell capable of expressing TNHX, PNHX, such as a cell selected from the group consisting of a seed (where appropriate), plant cell, bacterium, yeast, fungus, protozoa, algae, animal and animal cell.

Levels of nucleic acid molecule expression may be controlled with nucleic acid molecules or nucleic acid molecule fragments that code for anti-sense RNA inserted in the vectors described above.

*Agrobacterium tumefaciens*-mediated transformation, particle-bombardment-mediated transformation, direct uptake, microinjection, coprecipitation and electroporation-mediated nucleic acid molecule transfer are useful to transfer a $Na^+/H^+$ transporter nucleic acid molecule into seeds (where appropriate) or host cells, preferably plant cells, depending upon the plant species. The invention also includes a method for constructing a host cell capable of expressing a nucleic acid molecule of the invention, the method comprising introducing into said host cell a vector of the invention. The genome of the host cell may or may not also include a functional TNHX or PNHX gene. The invention also includes a method for expressing a TNHX or PNHX transporter polypeptide in the host cell or a plant, plant part, seed or plant cell of the invention, the method comprising culturing the host cell under conditions suitable for gene expression. The method preferably also includes recovering the expressed polypeptide from the culture.

The invention includes the host cell comprising the recombinant nucleic acid molecule and vector as well as progeny of the cell. Preferred host cells are fungal cells, yeast cells, bacterial cells, mammalian cells, bird cells, reptile cells, amphibious cells, microorganism cells and plant cells. Host cells may be cultured in conventional nutrient media. The media may be modified as appropriate for inducing promoters, amplifying genes or selecting transformants. The culture conditions, such as temperature, composition and pH will be apparent. After transformation, transformants may be identified on the basis of a selectable phenotype. A selectable phenotype can be conferred by a selectable marker in the vector.

Transgenic Plants and Seeds

Plant cells are useful to produce tissue cultures, seeds or whole plants. The invention includes a plant, plant part, seed, or progeny thereof including a host cell transformed with a PNHX nucleic acid molecule. The plant part is preferably a leaf, a stem, a flower, a root, a seed or a tuber.

The invention includes a transformed (transgenic) plant having increased salt tolerance, the transformed plant containing a nucleic acid molecule sequence encoding for $Na^+/H^+$ transporter polypeptide activity and the nucleic acid molecule sequence having been introduced into the plant by transformation under conditions whereby the transformed plant expresses a $Na^+/H^+$ transporter in active form.

The methods and reagents for producing mature plants from cells are known in the art. The invention includes a method of producing a genetically transformed plant which expresses PNHX or TNHX polypeptide by regenerating a genetically transformed plant from the plant cell, seed or plant part of the invention. The invention also includes the transgenic plant produced according to the method. Alternatively, a plant may be transformed with a vector of the invention.

The invention also includes a method of preparing a plant with increased salt tolerance, the method comprising transforming the plant with a nucleic acid molecule which encodes a TNHX transporter polypeptide, a PNHX transporter polypeptide or a polypeptide encoding a $Na^+/H^+$ transporter polypeptide capable of increasing salt tolerance in a cell, and recovering the transformed plant with increased salt tolerance. The invention also includes a method of preparing a plant with increased salt tolerance, the method comprising transforming a plant cell with a nucleic acid molecule which encodes a TNHX transporter polypeptide, a PNHX transporter polypeptide or a polypeptide encoding a $Na^+/H^+$ transporter polypeptide capable of increasing salt tolerance in a cell, and producing the transformed plant with increased salt tolerance.

Overexpression of $Na^+/H^+$ exchangers leads to an improved ability of the transgenic plants to uptake more monovalent cations from the growth media (soil) leading to an increased or enhanced tissue expansion. Therefore, the invention also relates to methods of producing or growing plants with increased tissue expansion (this could be manifested as enhanced size, growth or growth potential and may appear as increased or enhanced root, crown, shoot, stem, leaf, flower size or abundance in comparison to a wild type plant). The methods of preparing plants that have increased tissue expansion are the same as the methods for preparing a plant with increased salt tolerance described in this application (or the methods are easily adapted, to the extent that there is a difference in the methods).

The plants whose cells maybe transformed with a nucleic acid molecule of this invention and used to produce transgenic plants include, but are not limited to the following:

Target Plants.

Group I (Transformable Preferably via *Agrobacterium tumefaciens*)
Arabidopsis
Potato
Tomato
Brassica
Cotton
Sunflower
Strawberries
Spinach
Lettuce
Rice Group II (Transformable Preferably via Biolistic Particle Delivery Systems (Particle Bombardment)
Soybean
Rice
Corn
Wheat
Rye
Barley
Atriplex
Salicornia The nucleic acid molecule may also be used with other plants such as oat, barley, hops, sorgum, alfalfa, sunflower, alfalfa, beet, pepper, tobacco, melon, squash, pea, cacao, hemp, coffee plants and grape vines. Trees may also be transformed with the nucleic acid molecule. Such trees include, but are not limited to maple, birch, pine, oak and poplar. Decorative flowering plants such as carnations and roses may also be transformed with the nucleic acid molecule of the invention. Plants bearing nuts such as peanuts may also be transformed with the salt tolerance nucleic acid molecule. Preferred plants are Alfalfa, Almond, Apple, Apricot, Arabidopsis, Artichoke, Atriplex, Avocado, Barley, Beet, Birch, Brassica, Cabbage Cacao, Cantaloup/cantalope, Carnations, Castorbean, Cauliflower, Celery, Clover, Coffee, Corn, Cotton, Cucumber, Garlic, Grape, Grapefruit, Hemp, Hops, Lettuce, Maple, Melon, Mustard, Oak, Oat, Olive, Onion, Orange, Pea, Peach, Pear, Pepper, Pine, Plum, Poplar, Potato, Prune, Radish, Rave, Rice, Roses, Rye, Sorghum, Soybean, Spinach, Squash, Strawberries, Sunflower, Sweet corn, Tobacco, Tomato and Wheat.

In a preferred embodiment of the invention, plant tissue cells or cultures which demonstrate salt tolerance are selected and plants which are salt tolerant are regenerated from these cultures. Methods of regeneration will be apparent to those skilled in the art (see Examples below, also). These plants may be reproduced, for example by cross pollination with a plant that is salt tolerant or a plant that is not salt tolerant. If the plants are self-pollinated, homozygous salt tolerant progeny may be identified from the seeds of these plants, for example by growing the seeds in a saline environment, using genetic markers or using an assay for salt tolerance. Seeds obtained from the mature plants resulting from these crossings may be planted, grown to sexual maturity and cross-pollinated or self-pollinated.

The nucleic acid molecule is also incorporated in some plant species by breeding methods such as back crossing to create plants homozygous for the salt resistance nucleic acid molecule.

A plant line homozygous for the salt tolerance nucleic acid molecule maybe used as either a male or female parent in a cross with a plant line lacking the salt tolerance nucleic acid molecule to produce a hybrid plant line which is uniformly heterozygous for the nucleic acid molecule. Crosses between plant lines homozygous for the salt resistance nucleic acid molecule are used to generate hybrid seed homozygous for the resistance nucleic acid molecule.

The nucleic acid molecule of the invention may also be used as a marker in transformation experiments with plants. A salt sensitive plant may be transformed with a salt tolerance nucleic acid molecule and a nucleic acid molecule of interest which are linked. Plants transformed with the nucleic acid molecule of interest will display improved growth in a saline environment relative to the non-transformed plants.

Fragments/Probes

Preferable fragments (fragments are also referred to as polypeptide fragments or peptide fragments) include 10 to 50, 50 to 100, 100 to 250, 250 to 500, 500 to 1000, 1000 to 1500, or 1500 or more nucleotides of a nucleic acid molecule of the invention. A fragment may be generated by removing a single nucleotide from a sequence of SEQ ID NOS: 1, 3, and/or 5 (or a partial sequence thereof). Fragments may or may not have $Na^+/H^+$ transporter activity.

The nucleic acid molecules of the invention (including a fragment of SEQ ID NOS: 1, 3, and/or 5 (or a partial sequence thereof) can be used as probes to detect nucleic acid molecules according to techniques known in the art (for example, see U.S. Pat. Nos. 5,792,851 and 5,851,788). The probes may be used to detect nucleic acid molecules that encode polypeptides similar to the polypeptides of the invention. For example, a probe having at least about 10 bases will hybridize to similar sequences under stringent hybridization conditions (Sambrook et al. 1989, Molecular Cloning, A Laboratory Manual, Cold Spring Harbor).

The invention includes oligonucleotide probes made from the AtNHX sequences described in this application or other nucleotide sequences of the invention. The probes may be about 10 to 30 or 15 to 30 nucleotides in length and are preferably at least 30 or more nucleotides. A preferred probe is 5'-TTCTTCATATATCTTTTGCCACCC-3' (SEQ ID NO: 7) (coding for the amiloride binding domain) or at least about 10 or 15 nucleotides of this sequence. The invention also includes an oligonucleotide including at least 30 consecutive nucleotides of an AtNHX molecule of SEQ ID NOS: 1, 3, and/or 5 (or a partial sequence thereof). The probes are useful to identify nucleic acids encoding AtNHX, polypeptides and proteins other than those described in the application, as well as peptides, polypeptides, and proteins have $Na^+/H^+$ transporter activity and preferably functionally equivalent to AtNHX. The oligonucleotide probes are capable of hybridizing to one or more of the of SEQ ID NOS: 1, 3, and/or 5 (or a partial sequence thereof) or the other sequences of the invention under low, moderate or high stringency hybridization conditions. A nucleotide sequence encoding a polypeptide of the invention may be isolated from other organisms by screening a library under low, moderate or high stringency hybridization conditions with a detectable probe (e.g. a labeled probe). The activity of the polypeptide encoded by the nucleotide sequence may be assessed by cloning and expression of the DNA. After the expression product is isolated, the polypeptide is assayed for $Na^+/H^+$ transporter activity as described in this application.

Functionally equivalent AtNHX, TNHX or PNHX nucleic acid molecules from other cells, or equivalent AtNHX, TNHX or PNHX-encoding cDNAs or synthetic DNAs, can also be isolated by amplification using Polymerase Chain Reaction (PCR) methods. Oligonucleotide primers, including degenerate primers, based on the amino acid sequence of SEQ ID NOS: 2, 4, or 6 (or a partial sequence thereof) can be prepared and used in conjunction with PCR technology employing reverse transcriptase to amplify functionally equivalent DNAs from genomic or cDNA libraries of other organisms. Alternatively, the oligonucleotides, including degenerate nucleotides, can be used as probes to screen cDNA libraries.

Thus, the invention includes an oligonucleotide probe comprising all or part of a nucleic acid of SEQ ID NOS: 1, 3, and/or 5 (or a partial sequence thereof), or a complementary strand thereof. The probe is preferably labeled with a detectable marker. The invention also includes an oligonucleotide comprising at least 10, 15 or 30 nucleotides capable of specifically hybridizing with a sequence of nucleic acids of SEQ ID NOS: 1, 3, and/or 5 (or a partial sequence thereof). The invention also includes a single strand DNA primer for amplification of PNHX nucleic acid, wherein the primer is selected from a nucleic acid sequence derived from a nucleic acid sequence of SEQ ID NOS: 1, 3, and/or 5 (or a partial sequence thereof).

The invention also includes a method for identifying nucleic acid molecules encoding a TNHX, PNHX or AtNHX polypeptide. Techniques for performing the methods are described in, for example, U.S. Pat. Nos. 5,851,788 and 5,858,719. A preferred method includes contacting a sample containing nucleic acids with an oligonucleotide, wherein said contacting is effected under low, moderate or high stringency hybridization conditions, and identifying nucleic acids which hybridize thereto. Hybridization forms a hybridization complex. The presence of a complex correlates with the presence of a nucleic acid molecule encoding TNHX, plant PNHX polypeptide or AtNHX in the sample. In a preferred method, the nucleic acid molecules are amplified by the polymerase chain reaction prior to hybridization.

Kits

The invention also includes a kit for conferring increased salt tolerance to a plant or a host cell including a nucleic acid molecule of the invention (preferably in a composition of the invention) and preferably reagents for transforming the plant or host cell.

The invention also includes a kit for detecting the presence of a TNHX or a PNHX nucleic acid molecule, comprising at least one of oligonucleotide of the invention. Kits may be prepared according to known techniques, for example, see U.S. Pat. Nos. 5,851,788 and 5,750,653.

Antibodies

The invention includes an isolated antibody immunoreactive with a polypeptide of the invention (see Example 1). The antibody may be labeled with a detectable marker or unlabeled. The antibody is preferably a monoclonal antibody or a polyclonal antibody. TNHX, PNHX or AtNHX antibodies can be employed to screen organisms containing TNHX, PNHX or AtNHX polypeptides. The antibodies are also valuable for immunopurification of polypeptides from crude extracts.

The isolated antibody is preferably specifically reactive with a TNHX or PNHX transporter, preferably an AtNHX transporter. The transporter is preferably encoded by a nucleic acid molecule of SEQ ID NOS: 1, 3, and/or 5 (or molecules that hybridize to a molecule of SEQ ID NOS: 1, 3, and/or 5 under low, moderate or high stringency hybridization conditions or molecules having at least about: 17%, at least 20%, at least 25%, or at least 35% sequence identity (or the other preferred percentages of identity or sequence similarity described above) to a molecule of SEQ ID NOS: 1, 3, and/or 5 (or a partial sequence thereof). The transporter is preferably a polypeptide of SEQ ID NOS: 2, 4, and/or 6 (or polypeptides having at least about: 28%, 35% sequence identity (or the other preferred percentages of identity or sequence similarity described above) to a polypeptide of SEQ ID NOS: 2, 4, and/or 6 (or a partial sequence thereof). The antibody preferably does not cross-react with other transporter polypeptides. The antibody is preferably specifically reactive with a polypeptide having an amino acid sequence encoded by SEQ ID NOS: 1, 3, and/or 5 (or a partial sequence thereof).

Examples of the preparation and use of antibodies are provided in U.S. Pat. Nos. 5,792,851 and 5,759,788. For other examples of methods of the preparation and uses of monoclonal antibodies, see U.S. Pat. Nos. 5,688,681, 5,688,657, 5,683,693, 5,667,781, 5,665,356, 5,591,628, 5,510,241, 5,503,987, 5,501,988, 5,500,345 and 5,496,705. Examples of the preparation and uses of polyclonal antibodies are disclosed in U.S. Pat. Nos. 5,512,282, 4,828,985, 5,225,331 and 5,124,147.

The invention also includes methods of using the antibodies. For example, the invention includes a method for detecting the presence of TNHX, PNHX or AtNHX transporter polypeptide, by: a) contacting a sample containing one or more polypeptides with an antibody of the invention under conditions suitable for the binding of the antibody to polypeptides with which it is specifically reactive; b) separating unbound polypeptides from the antibody; and c) detecting antibody which remains bound to one or more of the polypeptides in the sample.

Research Tool

Cell cultures, seeds, plants and plant parts transformed with a nucleic acid molecule of the invention are useful as research tools. For example, one may obtain a plant cell (or a cell line, such as an immortalized cell culture or a primary cell culture) that does not express AtNHX1, insert an AtNHX1 nucleic acid molecule in the cell, and assess the level of AtNHX1 expression and activity. Alternatively, PNHX nucleic acid molecules may be overexpressed in a plant that expresses a PNHX nucleic acid molecule. In another example, experimental groups of plants may be transformed with vectors containing different types of PNHX nucleic acid molecules (or PNHX nucleic acid molecules similar to PNHX or fragments of PNHX nucleic acid molecules) to assess the levels of protein produced, its functionality and the phenotype of the plants (for example, phenotype in saline soil). The polypeptides are also useful for in vitro analysis of TNHX, PNHX or AtNHX activity or structure. For example, the polypeptides produced can be used for microscopy or X-ray crystallography studies.

The TNHX, PNHX or AtNHX nucleic acid molecules and polypeptides are also useful in assays. Assays are useful for identification and development of compounds to inhibit and/or enhance polypeptide function directly. For example, they are useful in an assay for evaluating whether test compounds are capable of acting as antagonists for PNHX polypeptides by: (a) culturing cells containing: a nucleic acid molecule which expresses PNHX polypeptides (or polypeptides having PNHX or $Na^+/H^+$ activity) wherein the culturing is carried out in the presence of: increasing concentrations of at least one test compound whose ability to inhibit transport activity of PNHX polypeptide is sought to be determined, and a fixed concentration of salt; and (b) monitoring in the cells the level of salt transported out of the cytosol as a function of the concentration of the test compound, thereby indicating the ability of the test compound to inhibit PNHX transporter activity. Alternatively, the concentration of the test compound may be fixed and the concentration of salt may be increased.

Another experiment is an assay for evaluating whether test compounds are capable of acting as agonists for PNHX polypeptide characterized by being able to transport salt across a membrane, (or polypeptides having PNHX or $Na^+/H^+$ transporter activity) by (a) culturing cells containing: a nucleic acid molecule which expresses PNHX polypeptide or (or polypeptides having PNHX activity) thereof, wherein said culturing is carried out in the presence of: fixed concentrations of at least one test compound whose ability to increase or enhance salt transport activity of PNHX polypeptide is sought to be determined, and an increasing concentration of salt; and (b) monitoring in the cells the level of salt transported out of the cytosol as a function of the concentration of the test compound, thereby indicating the ability of the test compound to increase or enhance PNHX polypeptide activity. Alternatively, the concentration of the test compound may be fixed and the concentration of salt may be increased. Suitable assays may be adapted from, for example, U.S. Pat. No. 5,851,788. It is apparent that TNHX and AtNHX may also be used in assays.

Bioremediation

Soils containing excessive salt may be unable to grow plants in a manner suitable for agriculture. The invention includes a method for removing salt from a growth medium, comprising growing a plant transformed with a nucleic acid molecule of the invention and expressing a salt tolerance $Na^+/H^+$ transporter polypeptide in the growth medium for a time period sufficient for the plant root to uptake and accumulate salt in the root or shoot biomass. The growth medium may be a solid medium, semi-solid medium, liquid medium or a combination thereof. It may include soil, sand, sludge, compost, or artificial soil mix. The shoot (leaf or stem) or and root biomass may be harvested. Preferably, a sufficient portion of the shoot biomass is not harvested and is left in the growth media to permit continued plant growth.

Using Exogenous Agents in Combination with a Vector

The nucleic acid molecules of the invention may be used with other nucleic acid molecules that relate to salt tolerance, for example, osmoregulant genes. Host cells or plants may be transformed with these nucleic acid molecules. Osmoregulants are disclosed, for example, in U.S. Pat. Nos. 5,563,324 and 5,639,950. The following Examples are intended to illustrate and assist in the further understanding of the invention. Particular materials employed, species, conditions and the like are not intended to limit the reasonable scope of the invention.

EXAMPLE 1

Preparation of Polyclonal and Monoclonal Antibodies.

Hydropathy profiles of the *Arabidopsis* $Na^+/H^+$ antiport revealed a relatively hydrophilic domain (at the C-terminus) with possible regulatory functions. The C-terminus was sub-cloned into the pGEX-2TK vector (Pharmacia) to allow the overexpression of the C-terminus polypeptide as a GST-fusion polypeptide in *E. coli*. The fusion polypeptide was purified by glutathione-affinity chromatography and used as an antigen in rabbits to obtain polyclonal antibodies (30).

Monoclonal antibodies are prepared in mice hybridomas according to established techniques (30) using the C-terminus polypeptide as described above. Polyclonal and monoclonal antibodies raised against other regulatory regions of the *Arabidopsis* $Na^+/H^+$ antiport are also obtained as described above. The invention includes the antibodies and the hybridoma which secretes the monoclonal antibodies.

EXAMPLE 2

Identification of Homologous Nucleic Acid Molecules from other Plant Species, Preferably Salt Tolerant Species.

Several experimental approaches are used to identify homologous nucleic acid molecules from salt tolerant species. a) We screen cDNA and genomic libraries from sugar beets (a moderate salt-tolerant crop, also known as red beet) under low-stringency conditions with an *Arabidopsis* $Na^+/$ H+ antiport cDNA as a probe (31); b) We apply PCR techniques using degenerate oligonucleotide primers designed according to the conserved regions of the *Arabidopsis* Na+/H+ antiport (32); c) We screen cDNA expression libraries from different plants (salt-tolerant and salt-sensitive) using antibodies raised against an *Arabidopsis* Na+/H+ antiport (31). We also use bioinformatics techniques to identify nucleic acid molecules. The invention includes methods of using such a nucleic acid molecule, for example to express a recombinant polypeptide in a transformed cell.

The techniques described above for isolating nucleic acid molecules from *Arabidopsis* and sugar beet are used to isolate a salt tolerance nucleic acid molecule from *Atriplex* and other plants.

EXAMPLE 3

Overexpression of the PNHX Transporter Preferably *Arabidopsis* Transporter (AtNHX).

The Na+/H+ antiport is expressed in *Arabidopsis* plants, although the wild type plants show impaired growth at NaCl concentrations higher than 75 mM. The Na+/H+ antiport is overexpressed in these plants in order to improve their tolerance to high salt concentrations. A full length cDNA (preferably coding for the AtNHX1 polypeptide (AtNHX2, AtNHX3 or AtNHX4) cloned from an *Arabidopsis thaliana* (Columbia) seedling cDNA library is ligated into a pB1NS1 vector (33). This vector contains a constitutively strong promotor ("super-promotor" (20)). Also, T-DNA vectors (pBECKS) are used (34). Constructs containing the AtNHX1 cDNA with the full Na+/H+ antiport open reading frame in a sense orientation were selected by colony hybridization using the AtNHX1 as a probe and by restriction-digest analysis using BglII restriction endonuclease. These constructs are used to transform *Agrobacterium tumefaciens*, and these transformed *Agrobacterium tumefaciens* are used for transformation of *Arabidopsis* plants. The *Agrobacterium* for inoculation is grown at 28° C. in a medium containing 5 g/l Bacto Beef Extract, 5 g/l Bacto-Peptone, 1 g/l Bacto Yeast Extract, 240 mg $MgSO_4$ and 5 g/l sucrose. The pH will be adjusted to 7.2 with NaOH.

*Arabidopsis* seeds are washed and surface-sterilized in 5% (w/v) sodium hypochlorite containing 0.15% (v/v) Tween-20. The seeds are rinsed thoroughly with sterile distilled water. Seed aliquots are dispensed in flasks containing 45 ml of cocultivation medium (MS salts, 100 mM sucrose, 10 mg/l thiamine, 0.5 mg/l pyridoxine, 0.5 mg/l nicotinic acid, 100 mg/l inositol and the pH adjusted to 6.0 with KOH. The flasks are incubated at 22° C. under constant rotation (190 rpm) and constant light. After 10-18 h (time needed to break clumps of seeds) 5 ml of log phase of *Agrobacterium* ($OD_{600}$=0.75) carrying the AtNHX1 construct are added. Twenty-four hours following the inoculation, the seeds are dried by filtration and sown into pre-soaked vermiculite. The flats containing the seeds are irrigated as required with a half-Hoagland solution. The flats are covered with plastic to prevent desiccation and maintained at low artificial illumination. After 3 days the flats are transferred to the greenhouse (the plastic cover removed) under a 16/8 day/night cycle. Supplementary light is provided by high pressure sodium vapor lights. Seven weeks after sowing, the plants are dried thoroughly and the seeds (T2) harvested. Transformation efficiency is estimated by plating 100,000 seeds (approximately 2.5 g of seeds) on agar plates containing 50 mg/l kanamycin in a medium containing 1% (w/v) sucrose, 0.8 (w/v) agar, MS salts and a pH 6.0 adjusted with KOH. The plates are transferred to a growth room at 25° C. under continuous light. After 10 days the kanamycin-resistant seedlings are transferred to new growth medium for 2 weeks and then transferred to small pots containing vermiculite. At senescence (8 weeks) the seeds are collected from single plants (T3). These seeds are germinated and used to assess salt tolerance of the transgenic plants.

EXAMPLE 4

Overexpression of TNHX or PNHX in other Plants.

In a preferred method, overexpression of PNHX, preferably AtNHX2, AtNHX4, or AtNHX5, in a number of plants (potato, tomato, brassica, cotton, sunflower, strawberries, spinach, lettuce, rice, soybean, corn, wheat, rye, barley, atriplex, salicornia, and others) is achieved by *Agrobacterium tumefaciens*-based transformation and/or particle bombardment (AtNHX2, AtNHX4, AtNHX5 are also useful in this example). The full length cDNA (coding for the AtNHX2, 4 or 5) is ligated into the pBINS1 vector or pBECKS (as described above) and these constructs are used to transform *Agrobacterium tumefaciens* strain LBA4404. *Agrobacterium* used for inoculation is grown as described above. Cultured cells (callus), leaf explants, shoot and root cultures are used as targets for transformation. The targeted tissues are co-cultivated with the bacteria for 1-2 days. Afterwards, the tissue is transferred to a growth media containing kanamycin. After one week the tissue is transferred to a regeneration medium containing MS salts, 1% sucrose, 2.5 mg/l 3-benzyladenine, 1 mg/l zeatin, 0.75% agar and kanamycin. Weekly transfers to fresh regeneration media are performed.

In another preferred embodiment, overexpression constructs carrying the AtNHX2, 4 or 5 cDNAs are introduced into an electro-competent *Agrobacterium tumefaciens* (LBA4404) by electroporation. The *Agrobacteria* are plated on LB plates containing 50 mg/L kanamycin and grown for 2 days at 30° C. to select for bacteria carrying the overexpression constructs. One liter liquid LB+kanamycin (50 mg/L) is inoculated with a single *Agrobacterium* colony selected from the LB (kanamycin 50 mg/L) plates. The culture is grown to a minimum of OD=1 (600 nm) for 2-3 days. The Agrobacteria are then pelleted and resuspended in 1L infiltration medium (1M -0.5XMS salts; 0.5 g/L MES; 5% sucrose; 0.03% Silwet L-77). Flowering *Arabidopsis* plants with primary bolts reaching ~15 cm are used for the transformation procedure (T1). Pots of *Arabidopsis* plants are dunked into the 1M solution containing the *Agrobacteria* and left submerged for 2-6 minutes. The same procedure can be repeated after 8-12 days on the same plants. Plants are allowed to senesce, the plants are dried thoroughly and the seeds harvested. Seeds are plated on agar plates containing 25 mg/L kanamycin in a medium containing MS salts, 0.8% (w/v) agar adjusted to pH 6.0 with KOH. The plates are transferred to a growth room at 25° C. under continuous light. After 10 days the kanamycin-resistant seedlings (T2) are transferred to small pots containing vermiculite. At senescence (~8 weeks) the seeds are collected from single plants and plated on agar plates containing MS salts and 25 mg/L kanamycin. After 10 days the kanamycin-resistant seedlings (T3) are transferred to small pots containing vermiculite. Seeds produced by these plants are germinated and used to assess salt tolerance of the transgenic plants. A biolistic particle delivery system (particle bombardment) is also used for the overexpression of NHX (AtNHX2, AtNHX4, or AtNHX5 are useful for this example). Constructs made using a plasmid vector preferably carrying a constitutive promoter, the AtNHX2, 4 or 5 open reading frame in a sense orientation and a NOS termination site are used. Plasmid DNA is precipitated into 1.25 mg of 1-2 µm gold particles using 25 µl of 2.5 M CaCl$_2$ and 10 µl of 0.1 M thiamine (free base). DNA-coated particles are washed with 125 lµl of 100% ethanol and then resuspended in 30 µl ethanol. The samples are sonicated to obtain an efficient dispersion, and the samples are aliquoted to obtain delivery disks containing 3 µg of DNA each. Particle bombardment is optimized according to the specific tissue to be transformed. Tissue samples are placed in Petri dishes containing 4.5 g/l basal MS salts, 1 mg/l thiamine, 10 mg/l myoinositol, 30 g/l sucrose, 2.5 mg/l amphotericin and 10 mM K$_2$HPO$_4$ at pH 5.7. After bombardment the petri dishes are incubated for 18-24 hours. Tissue is regenerated in plates with growth media containing the selective marker. Rooting is initiated and transformed plants are grown under optimal growth conditions in growth chambers. After 2-4 weeks the seedlings are transferred to new growth medium for 2 weeks and then transferred to small pots containing vermiculite. At senescence the seeds are collected from single plants. These seeds are germinated and used to assess salt tolerance of the transgenic plants.

EXAMPLE 5

Overexpression of AtNHX2, 4 or 5 Homologs in other Plants.

Overexpression of AtNHX2, 4 or 5 homologs from other plant species, preferably salt tolerant species (i.e., sugar beet) in other plants (potato, tomato, brassica, cotton, sunflower, strawberries, spinach, lettuce, rice, soybean, corn, wheat, rye, barley, atriplex, salicornia, and others) is achieved by *Agrobacterium tumefaciens*-based transformation and/or particle bombardment as described above (in Examples 3 and 4). Regeneration of the transformed plants is performed as described in Examples 3 and 4.

EXAMPLE 6

Expression of AtNHX2, 4 or 5, Homologs and Derivatives in *Saccharomyces cerevisiae*.

Expression of TNHX or PNHX, preferably AtNHX1, AtNHX2, 4 or 5 homologs and derivatives in yeast is useful to assess and characterize the biochemical properties of the recombinant and native polypeptides. Expression in yeast also facilitates the study of interactions between AtNHX1, its homologs and derivatives with regulatory polypeptides. We have made conditional expression constructs by ligating the coding region of the AtNHX2, 4 or 5 cDNA into two vectors, pYES2 (Invitrogen) and pYEP434 (35). Both constructs provide galactose-inducible expression, but pYES2 has a URA3 selectable marker while pYEP434 has LEU2 as a selectable marker. Transformation by lithium acetate (36), 1994), is followed by selection on solid media containing amino acids appropriate for the selection of cells containing the transformation vector. For integrative transformation, the YXplac series of vectors for integrative transformation are used (37).

EXAMPLE 7

Molecular Characterization and Functional Analysis of Na$^+$/H$^+$ Exchangers from *Arabidopsis* and other Plants, Preferably Salt-Tolerant (Halophytes) Plants.

We do molecular and biochemical characterization of the different Na$^+$/H$^+$ exchangers from *Arabidopsis* and other plants, preferably salt tolerant plants (halophytes). We determine the expression patterns of the different *Arabidopsis* putative exchangers. Using Northern blot analysis with isoform-specific cDNA probes under high stringency conditions and standard molecular biology protocols, we determine the tissue-specificity, developmental and salt-inducibility gene expression profiles of each isoform.

We employ common molecular biology procedures to isolate Na$^+$/H$^+$ exchangers from other plants as described below, in particular halophytes (such as *Beta vulgaris, Atriplex, Messembryanthemum chrystalinum*, etc.). We designed degenerate oligonucleotide PCR primers, based upon highly conserved regions within Na$^+$/H$^+$ exchangers (one within the amiloride-binding domain, and another within a region about 200 amino acid residues further downstream) from *Arabidopsis*, yeast, mammals, and *C. elegans*, to generate a 600-1,000 by DNA fragments by PCR. Sequencing of these products revealed significant homology to AtNHX1 and they are therefore being used as a probe to screen the different halophyte cDNA libraries to isolate the full-length cDNAs by standard methods. We use the nucleic acid molecules obtained in this procedure in methods of producing transgenic host cells and plants as described above.

We have subcloned unique regions from AtNHX1, AtNHX2 and AtNHX3 isoforms into a prokaryotic expression vector (pGEX2TK, Pharmacia) for the production of recombinant GST-fusion proteins that are being used for the generation of isoform-specific polyclonal antibodies in rabbits. Briefly, sequence-specific oligonucleotides, with 5' BamHI (sense strand) and 3' EcoRI (antisense strand) flanking restriction sites, were used for PCR-mediated amplification of the unique (partial) coding regions from each isoform, and the digested PCR products were ligated into EcoRI/BamHI-digested pGEX2TK vector. pGEX2TK plasmids containing the inserts corresponding to each AtNHX isoform were sequenced on both strands to verify the fidelity of the PCR reaction and were used for expression and purification of the recombinant GST-fusion proteins in *E. coli* (BL21pLysS) as per manufacturers instructions (Pharmacia). We follow an identical procedure to that described above to produce recombinant halophyte-PNHX GST-fusion protein in *E. coli*. Antibodies against the fusion proteins are produced in rabbits by standard procedures and their isoform-specificity are confirmed by western blotting using the different GST-fusion proteins. The antibodies are used in conjunction with subcellular membrane fractions (prepared from sucrose density gradients) (15) from various *Arabidopsis* and other plant tissues, preferably halophyte tissues and western blots to determine the subcellular localization of each Na$^+$/H$^+$ exchanger isoform. These localization studies assign functions to the various isoforms.

EXAMPLE 8

Biochemical Characterization and Functional Analysis of Na$^+$/H$^+$ Exchangers from *Arabidopsis* and other Plants, Preferably Salt-Tolerant (Halophytes) Plants.

Biochemical characterization of the Na$^+$/H$^+$ exchanger isoforms is performed in (i) heterologous eukaryotic expression systems (baculovirus expression system in Sf9 insect cells, transgenic yeast); and in (ii) transgenic plants.

The use of heterologous expression systems allows the fast characterization of the kinetic properties of each exchanger isoform ($K_m$, $V_{max}$, ion specificity). Baculovirusinfected Sf9 cells have proven to be a useful and adaptable system for high-level expression of correctly folded eukaryotic membrane proteins, thus they are an ideal tool for the study of membrane-bound proteins. The large size of the cells, combined with the relatively short time needed for the expression of the foreign plasma membrane-bound proteins (3-4 days) provides an excellent experimental system for the application of isotope exchange techniques. For expression in Sf9 insect cells, the Invitrogen baculovirus Sf9 insect cell system is used. Expression vector constructs (pBluBac4.5, Invitrogen) encoding full-length AtNHX exchanger proteins are prepared for each AtNHX and other PNHX isoforms using a PCR-based subcloning approach similar to that described above for the generation of GST-fusion proteins. Initially, the suitability of the insect cell expression system for uptake analysis is performed using a single AtNHX isoform. The other PNHX isoforms are studied in a similar manner. Cultures of Sf9 insect cells are infected with baculovirus containing expression vector constructs encoding the different PNHX isoforms. Infection and selection of transformants are performed as per manufacturer's instructions (Invitrogen). The isoform-specific antibodies described above aid in the assessment of recombinant protein expression and localization within the insect cells.

Equally important is the use of transgenic yeast as a tool for the expression of recombinant eukaryotic proteins, particularly because of post-translational modifications and targeting to endomembranes. In addition, functional complementation of yeast mutant strains with plant proteins is often possible. We have subcloned the AtNHX1 cDNA into a yeast expression vector (pYES2) using a PCR-based approach as described above. Yeast (strain w303a) have been transformed with this construct and expression of the recombinant plant protein is confirmed once the antiserum is available. In addition, salt-tolerance of transformed yeast is assessed for each AtNHX isoform by comparing growth rates at different NaCl concentrations. Methods for the isolation of transport-competent plasma membranes and tonoplast and the isolation of intact vacuoles are performed. The kinetics of $H^+/Na^+$ exchange is measured in intact insect cells and yeast, intact yeast vacuoles, and isolated plasma membranes and tonoplast vesicles according to known methods. $Na^+$ influx in intact cells is monitored by isotopic exchange using ($^{22}Na^+$)Cl and fast-filtration techniques (17, i,ii). Kinetics of $H^+$-dependent $Na^+$ fluxes in vesicles is monitored by following the pH-dependent fluorescent quench of acridine dyes (13,17).

The results of these kinetic characterization studies provides information about the ion specificity, affinity, and optimal activity conditions for each AtNHX isoform. We assign the activity of each isoform to the corresponding target membrane, and we also determine which of the isoforms have a higher affinity for sodium. We characterize the mechanisms of salt tolerance in general and tissue-specificity and developmental expression in particular.

In transgenic plants, expression of the different $Na^+/H^+$ antiports is verified with western blots using the isoform-specific antibodies described above. The kinetics of $H^+/Na^+$ exchange is measured in intact vacuoles, isolated plasma membranes and tonoplast vesicles (from roots and leaves) as described above.

EXAMPLE 9

Identification of Positive and Negative Regulators of $Na^+/H^+$ Antiport Activity.

Heterologous expression of plant transport molecules in *Saccharomyces cerevisiae* has been used successfully in recent years in numerous studies. The availability of yeast mutants with salt-sensitive phenotypes (generated by 'knock-outs' of sodium transport molecules such as Δena1-4—the plasma membrane $Na^+$—ATPase pumps) makes it an especially suitable system for the study of sodium transport molecules. This heterologous expression facilitates kinetic studies of the antiport activity in yeast cells using radiolabelled $^{22}Na^+$.

Successful suppression of yeast mutants, incapable of sodium detoxification allows for the genetic identification of positive and negative regulators of these $Na^+/H^+$ antiports. Mutant yeast cells having a suppressed phenotype as a result of the expression of a plant $Na^+/H^+$ antiport are transformed with an *Arabidopsis* cDNA library for the purpose of identifying particular regulators of these antiport molecules. A phenotype of increased sodium tolerance in yeast identifies particular positive regulators of the antiport activity while negative regulators are identified by a phenotype of decreased sodium tolerance. These phenotypes depend on the co-expression of the particular cDNAs identified along with that of the $Na^+/H^+$ antiport under investigation. Identification of essential amino acid residues regulating the activity of $Na^+/H^+$ exchanger molecules is investigated by random mutagenesis of the antiport molecule which is achieved by PCR using a commercially available low fidelity Taq enzyme. The constructs generated are used in transforming sodium-related yeast mutants to identify particular $Na^+/H^+$ antiport residues that affect suppression of the mutant yeast phenotype. Both gain-of-function and loss-of-function mutations are examined and mapped to the particular mutant residue by sequencing. Gain-of-function mutations are of particular interest since they represent constitutive activation of the antiport activity allowing for increased sodium detoxification.

EXAMPLE 10

Transformation of *Arabidopsis thaliana* using Overexpression of Different Putative Isoforms and Antiports from other Plants, Preferably Salt Tolerant Plants and Evaluation of Salt-Tolerance

*Arabidopsis* represents a readily transformable model organism with the particular advantage of having a short generation time. *Agrobacterium tumefaciens*-mediated genetic transformation is utilized for *Arabidopsis* (ecotype Columbia). Studies include the overexpression of PNHX transgenes in a wild-type background, combined overexpression of more than one PNHX transgene, and suppression of endogenous PNHX expression using antisense PNHX expression. Stable transformation of progeny is confirmed by Southern blotting. Overexpression of transgenes, or suppression of expression using antisense constructs, is confirmed by Northern and western blotting. In all cases, salt-tolerance of transgenic plants is compared to wild-type plants, and control plants transformed with empty transformation vectors. Separate transformations are performed on *Arabidopsis* plants using expression vector constructs for each of the different AtNHX isoforms. In addition, *Arabidopsis* plants are transformed with PNHX genes from other plants, preferably salt tolerant plants in order to assess the effect on salt tolerance of the expression of a $Na^+/H^+$ exchanger in a glycophytic plant.

For overexpression studies, full-length AtNHX2, AtNHX4, and AtNHX5 cDNAs are subcloned in a sense orientation into the expression vector containing a "super-promoter" (20). A PCR based subcloning strategy is used for each AtNHX cDNA as described above for the production of NHXGST-fusion constructs. For the production of vector constructs containing PNHX cDNAs in an antisense orientation, oligonucleotides with SalI and SacI restriction sites flanking the C-terminal and N-terminal PNHX regions respectively, are used for PCR amplification. All plasmid constructs are sequenced on both strands to confirm the fidelity of the PCR amplification before transformation of *Agrobacterium tumefaciens* (strain LBA4404). For each PNHX-pBISN1 construct, approximately 1 L of *Agrobacterium* culture, grown under antibiotic selection at 28° C., is used for the transformation of *Arabidopsis*. Plants are ready for transformation when primary bolts are approximately 15 cm. About 2 flats of plants (~80 plants per flat) are used per transformation. A highly efficient, vacuum-less infiltration transformation method (iii) is used. Harvested *Agrobacterium* cultures are resuspended in an infiltration media containing a mild surfactant (Silwet L-77, Lehle Seeds), and each pot of *Arabidopsis* is simply submerged in the *Agrobacterium* for 2-6 minutes. Plants are thereafter drained, and returned to the growth chamber until the seeds are ready for harvesting (about 4 weeks). Seeds (T1 generation) are collected and after surface sterilization, are plated on sterile, selective media containing kanamycin, vernalized, and then grown under optimal conditions. Healthy seedlings showing kanamycin resistance after about 7 days are transplanted to soil and the presence of the transgene confirmed by Southern blotting. Seeds from T1 transformants (i.e. T2 generation) are harvested, sown, and T2 plants used for Northern and western blotting to determine the expression patterns of the transgenes and PNHX proteins. Representative transgenic lines (e.g. showing low, medium, or high transgene expression) is used for studies of salt-tolerance. A similar approach is used for transformation of *Arabidopsis* with the PNHXs from other plants.

Salt tolerance is assessed by measuring the growth rate of the plants at increasing salt concentrations. Plant biomass, root/shoot ratios, tissue ion content is measured. Root and hypocotyl growth rates is measured and correlated with tissue water content of plants growing at different NaCl concentrations.

EXAMPLE 11

Transformation of Crop Plants with *A. thaliana* and/or other Exchangers Under Constitutive and Inducible Promoters and Evaluation of Salt-Tolerance.

a) *Agrobacterium tumefaciens*-Mediated Transformation of Crop Plants

We assess whether or not homologues of the AtNHX genes exist in the plant of choice. We use degenerate oligonucleotide PCR-primers (as described for other plants) and a cDNA library to isolate the full-length cDNA. The high efficiency *Agrobacterium*-mediated transformation method developed specifically for *Brassica* by Moloney et al (iv) is used to introduce and overexpress foreign nucleic acid molecules and/or overexpress the endogenous PNHX nucleic acid molecule in the crop plant(s). This method lakes advantage of the fact that cut cotyledonary petioles from, which are capable of undergoing organogenesis (i.e. generating explants), are very susceptible to *Agrobacterium* infection. Shortly after germination (~5 days) cotyledons are excised and imbedded into Murashige-Skoog medium (Gibco) enriched with benyzladenine. Expression vector constructs are prepared using a PCR-based subcloning approach as described above using the pCGN5059 binary plasmid (which employs the CaMV 35S promoter to drive constitutively high expression) engineered for gentamycin resistance (iv) and cDNAs of the various AtNHX clones and/or the halophyte PNHX clones, and the chosen plant PNHX clones. Excised cotyledons are infected with *Agrobacterium* cultures (strain EHA101), containing the vector construct of interest, by brief dipping and then co-cultivated with the *Agrobacterium* for a 72 h. Subsequently, cotyledons are transferred to regeneration medium containing gentamycin as the selective agent. After explant regeneration, and subculturing, on selective media (~4 weeks) explants are transferred to rooting medium and then into soil once a root mass has developed. Tissue samples are examined from growing plants to confirm transgene presence by Southern blotting as described above for the transformation of *Arabidopsis*. Transformed plants (T1 generation) are allowed to flower and set seed and these seeds are germinated (T2) under selective conditions and transformants used for expression analysis of the transgenes and evaluation of salt-tolerance as described above. Also, biochemical analysis of the plants is performed. These include, $Na^+/K^+$ ratios, sugar, amino acid and quaternary N-compounds. Salt-tolerance is also evaluated in fields trials.

b) Microprojectile Bombardment-Mediated Transformation of Crop Plants.

A microprojectile bombardment-mediated transformation of crop plants is used when *Agrobacterium tumefaciens*-mediated transformation is not successful. We assess whether or not homologues of the AtNHX genes exist in the plant of choice. We use degenerate oligonucleotide PCR-primers (as described above) and a cDNA library to isolate the full-length cDNA. Expression vector constructs, using the pBAR vector for high level expression of AtNHX or the halophyte PNHX or the endogenous PNHX from the plant of choice, are used in conjunction with the microprojectile bombardment system as described by Tomes et al. (v). Bombardment procedures is carried out in callus tissue. Plant calli are initiated by culturing immature embryos on Callus medium (vi). After about 2 weeks, friable calli that are growing rapidly are subcultured and grown for an additional 2 weeks and then used for transformation. Calli for transformation are transferred to fresh medium, incubated for 24 h and bombarded with tungsten microprojectiles carrying the pBARNHX vector construct. Bombardment conditions is performed according to manufacturer's instructions. Calli that show visible growth 10 days after bombardment are transferred to selective media (containing either Bialaphos or Ignite) in order to identify putative transformants. The growth of transformed plant calli on this selective media is continued for 3-4 months. Each putative stable transgenic event becomes apparent as a mass of friable embyogenic callus growing in the presence of the selection agent. Stable transformation is verified by Southern blots. Selected calli are transferred onto a regeneration medium (v), kept in the dark at 28° C. for 7 days and then transferred to growth chambers under a 16-h photoperiod until green shoots appear. Plantlets (1-2 cm long) are transferred to individual tubes containing germination medium to allow continued development. At the three to four leaf stage, plants are transferred to soil and into the greenhouse. At the eight-leaf stage, these plants are sprayed with 1% (w/v) Ignite herbicide to detect the presence of the BAR gene. This herbicide kills those plants not carrying the BAR gene. Confirmed transgenic plants (T1) are allowed to mature, flower, set seed, and seeds used for the production of T2 plants. Transgenic T2 plants are used for the evaluation of salt-tolerance as described above. Transgenic T2 and T3 plants are used in field trials for the evaluation of salt tolerance.

EXAMPLE 12

Cloning and Characterization of NX5

Material and Methods

Plant Material and Transformation:

Sterilized *Arabidopsis thaliana* seeds (Columbia) were grown either in soil directly or transferred to soil after germinating first on agar plates containing 0.5× Murashige and Skoog (MS) medium. The plants were grown under 12 hour light at a constant 22° C.

*Agrobacterium*-mediated transformation was used to generate transgenic *Arabidopsis* lines. *Agrobacterium* was resuspended in infiltration solution containing 0.5×MS salt, 0.5 g/l MES; 5% sucrose and 0.03% Silwet. Flowering plants with primary bolts reaching 15 cm were dunked into a bacterial solution for 5 min. The plants were re-transformed 12 days later.

Transgenic seeds were screened on ½ MS-Kanamycin (25 mg/l) medium (1/2 MS K25). These plates were placed under 24 hour light at 22° C. The salt tolerance of the transgenic lines was tested by either growing the seeds on ½ MS-K25 plates—containing 100 mM NaCl and 200 mM NaCl or watering the plants in soil with 100 and 200 mM NaCl.

*Arabidopsis* seeds were sterilized as following: 50 µl of seeds were washed with 1 ml 70% ethanol alcohol for 2 min, then incubated with 1 ml of sterilization solution with constant shaking for 10 min. The sterilization solution contained 6% bleach and 0.1% Tween 20. Then the seeds were washed 5 times with sterilized ddH$_2$O. Finally, the seeds were resuspended in 1 ml of 0.1% phytagar and chilled at 4° C. at least overnight to break the dormancy.

Cloning of AtNHX5

5'- and 3'-Rapid Amplification of cDNA Ends were used to clone the full length of AtNHX5. SMART-RACE cDNA Amplification Kit and Advantage2 PCR Enzyme System from CLONTECH were used. All reactions were performed according to the manufacturer instructions.

When compared with the conventional reverse transcription reactions, the RACE system provides a better mechanism for generating full-length cDNAs by using both the SMART II oligonucletide and MMLV reverse transcriptase (RT). This MMLV RT can add 3-5 residues of dC to the 3' end of the first-strand cDNA, and these oligo-dC are harnessed by the dG-residues of SMART II which serves as an extended primer for reverse transcription. Since the dc-tailing activity of RT is most efficient only when the enzyme has reached the end of the RNA template, the SMART II sequence is typically added only to complete first-strand cDNA, and this guarantees the formation of cDNA that has a maximum amount of 5'sequence if high quality RNA is used. Furthermore, the Advantage 2 polymerase Mix includes Advan Taq DNA polymerase, a minor amount of a proofreading polymerase, and Taq Start antibody to provide automatic hot-start PCR, so this enzyme system allows efficient, accurate, and convenient amplification of cDNA.

5'-RACE to Obtain the 5' End Start Codon of AtNHX5:

For the synthesis of first-strand cDNA (5'-RACE-ready cDNA), 1 µl (1.5 µg) of total RNA, 1 µl of 5'-CDs primer (from the kit), 1 µl of SMART II oligo (from the kit), and 2 µl of ddH$_2$O were mixed in a 0.5-ml PCR tube, and incubated at 70° C. for 2 min and placed on ice for 2 min. Then 2 µl of 5× first-strand synthesis buffer (from the kit), 1 µl of 20 mM DTT, 1 µl of 10 mM dNTPs and 1 µl of Superscript II (MMLV RT) were added to the tube. Incubation was carried out at 42° C. for 1.5 hour. The reaction was diluted by adding 100 µl of Tricine-EDTA buffer and the tube was heated at 72° C. for 7 min.

Tricine-EDTA buffer was used because this buffer can maintain pH at high temperature better than Tris-EDTA buffer. Tris-based buffer can lead to low pH conditions that can degree DNA.

For the 5'-RACE, an AtNHX5 specific 3'-primer, X5 REV, was designed, which is 5'-CCC CAA CCC CTG CAG ACA TTG AGC CAG C-3' (SEQ ID NO: 8). The PCR reaction was set up by combining the following: 5 µl of 10× advantage 2 PCR buffer, 1 µl of 10 mM dNTPs mix, 1 µl of 50× advantage 2 polymerase mix, 5 µl of 5'-RACE-ready cDNA, 5 µl of 10×UPM, 1 µl of X5REV, and 32 µl of PCR-grade ddH$_2$O. The PCR cycle included 1 cycle of 94° C. for 2 min; 32 cycles of 94° C. for 30 sec and 68° C. for 3 min; 1 cycle of 72° C. for 5 min. Negative control was done by adding no 5'-RACE-ready cDNA.

3'-RACE to Obtain the Full-Length of AtNHX5 Gene:

3'-RACE-ready cDNA was synthesized similarly to 5'-RACE-ready cDNA, except that 1 µl of 5'-CDs primer and SMART II oligo were replaced by 3'-CDs primer attached with SMART II oligo.

For 3'-RACE, an AtNHX5 specific 5' primer, X5-5'-RACE, was designed, which is 5'-GCT GAA TGG AGG AAG TGA TGA TTT CTC CGG TGG-3' (SEQ ID NO: 9). The 3'-RACE PCR reaction mixture included: 5 µl of 10× advantage 2 polymerase buffer, 1 µl of 10 mM dNTPs, 1 µl of 50× advantage 2 polymerase mix, 5 µl of 3'-RACE-ready cDNA, 1 µl of 5'-RACE primer, 5 µl of 10×UPM, and 32 µl of PCR-grade ddH$_2$O. Negative controls were obtained by adding no 3'-RACE-ready cDNA. PCR cycle included: 1 cycle of 94° C. for 2 min; 36 cycles of 94 ° C. for 30 sec and 72 ° C. for 3 min; 1 cycle of 72° C. for 7 min.

Preparation and Purification of Antibodies Raised Against the X5-GST Fusion Protein:

A specific region of 105 amino acids of ATNHX5 was chosen to make the X5-GST fusion protein.

First, the coding sequence of these 105 amino acids was obtained by PCR with AtNHX5 cDNA and a pair of designed primers, GST-X5F (5'-CCC GCG GAT CCG GTG CAC TTA TAT CAG C-3' (SEQ ID NO: 10)) and GST-X5R (5'-GGC GGA ATT CAC AAC ACT CCA AGT TCT G-3' (SEQ ID NO: 11)). Then this piece of DNA was cloned in frame into PGEX-2TK vector in the site of BamHI (5'-end) and E CoRI (3'-end).

*E. Coli* strain BL21 pLysS was used to express the fusion protein under 1 mM IPTG induction. The fusion protein was confirmed by Western blots with the anti-GST antibody. The *E. Coli* lysate was applied to a polyacrylamide gel, and then the fusion protein was cut off and subjected to electroelution, lyophilization and concentration measurement by dot blot.

For the $1^{st}$ injection of the rabbit, 200 µl (200 ug) of purified fusion protein was mixed by vortex with 200 µl Freund's complete adjuvant (ICN Biochemicals Inc.). For the $2^{nd}$, $3^{rd}$ and $4^{th}$ time injection, 250 µl (100-150 ug) of purified protein were mixed with equal volume of Freund's incomplete adjuvant (ICN Biochemicals Ivc.).

For the purification of the antibody, affinity strip blots were used. For making one PVDF strip, 100 µg purified protein (GST or X5-GST fusion protein) was loaded on a large well of a polyacrylamide gel. The strips were blocked with 5% milk-PBST for 1 or 2 hours and washed with PBST for 5 min three times before placed into the serum tube. The serum was firstly incubated with GST PVDF strips, and then with X5-GST fusion protein stripes, at 4° C. overnight. The strips were washed with PBST 5 times with 5 min each time, and then washed with 0.1×PBST three times. The antibody was eluted with 0.2 M Glycine freshly made, pH 2.5), and the pH of the antibody solution was adjusted to 7.5 immediately by adding 2M Tris. Usually in 0.5 ml serum, 0.5 ml 2×PBS was added, and 2 or 3 protein strips were used to bind the antibody. The purified antibody was stored at 4° C.

Yeast Complementation:

Yeast complementation was performed to test the function of AtNHX5. AtNHX5 ORF sequence was first obtained by PCR with AtNHX5 cDNA and a pair of primers, 5'-X5-yeast-new (5'-CGC TCC CCC GGG ATG GAG GAA GTG ATG ATT TCT CC-3' (SEQ ID NO: 12)) and 3'-X5-yeast-new (5'-GGA CGC GTC GAC CTA CTC CCC ATC TCC ATC TCC-3' (SEQ ID NO: 13)). The yeast mutant, Δnhx1 (nutrition type:trp-), was transformed with AtNHX5 ORF sequence cloned in a yeast expression vector pYpGE15 at the SmaI (5') and SalI (3') sites. The wild type yeast and Δnhx1 mutant transformed with empty pYpGE15 vector, were also used as controls.

Transformation of Yeast:

The lithium acetate transformation method was used for the transformation of yeast. Yeast mutant strain, Δnhx1, was streaked on a try-SD plate and incubated at 30° C. overnight. Several colonies were picked and resuspended in 1 ml of sterile ddH$_2$O. The yeast cells were centrifuged at 3500 rpm for 2 min. Yeast cells were washed with 300 μl of 100 mM LiAc, and finally resuspended in 150 μl of 100 mM LiAc (yeast competent cells). For transformation, 75 μl of the yeast competent cells were mixed with 5 μl of plasmid, 5 μl of 10 μg/μl of denatured single-stranded salmon sperm DNA and 300 μl of 40% PEG (in LiAc/TE), and then incubated at 30° C. for 30 min without shaking. The yeast cells were heat-shocked at 42° C. for 15 min to let the DNA go inside. Half the mixture was plated on a trp⁻-ura⁻-SD plate and the plate was incubated at 30° C. for 2 days.

Salt Tolerance Test of the Transformants:

For testing the salt tolerance of the transformants, the yeast cells were plated on APG medium with NaCl concentrations ranging from 200 to 500 mM, and pH 4.5 and 5.5. As controls, wild type yeast Δnhx1 mutant and transformed with an empty pYpGE 15 vector and plated on the same medium plate with equal amount of cells. In order to plate equal amount of cell of every kind of yeast strains, all of the transformed yeast strains were grown in 2 ml of trp⁻-ura⁻⁻ 2% glucose-SD medium for 3 days at 30° C., because at this point, all yeast cultures were saturated. Then dilutions of 10×, 100× and 1000× were made, and then 3 μl of each culture were plated on APG plates containing 200 mM, 300 mM, 400 mM, and 500 mM NaCl at pH 4.5 and pH 5.5. The plates were incubated at 30° C.

Semi-Quantitative RT-PCR:

RT-PCR is a highly sensitive and rapid method of detecting mRNA levels of a gene. It has been shown to be thousands of times more sensitive than the traditional RNA blot techniques (Chirgwin et al., 1979; Chomczynski and Sacchi, 1987). Thus RT-PCR is more useful in analysis of single-copy genes or lowly expressed genes. RT-PCR involves two enzymatic reactions: a reverse transcription by usually MMLV RT, and polymerase chain reaction. But it is difficult to get quantitative information with this technique due to the exponential nature of PCR. Under ideal or theoretical conditions, the amount of product always doubles after each cycle, but the rate of production will reach a plateau stage after a certain number of cycles. There are several factors which may affect the amplification efficiency, such as the impurity of the RNA sample, and the length of the amplified sequence. There may be additional factors that cause the tube-to-tube variation even when a master mix of reaction components is used. So, in order to get accurate information, several strategies have been used in a semi-quantitative RT-PCR, including using an appropriate amount of initial template, appropriate numbers of PCR cycle and an endogenous sequence which is known to be expressed constantly as a internal control. The internal control is amplified using a second pair of specific primers. Usually, a mini-southern blot is applied to detect the bands of the PCR products. The ratios of the amount of the target products and that of the endogenous control represent the mRNA level of a gene, and this is called normalization.

Usually, 2 μg of total RNA and 25 PCR cycle are used for semi-quantitative RT-PCR. The RT-PCR beads from Amersham Pharmacia Biotech. Inc. was used for this thesis. To each RT-PCR bead (provided in a tube), 45 μl of DEPC-H$_2$O were added and dissolved on ice. Then 1 μl of Oligo dT (0.5 ug/ul), 0.5 μl of each of the four following primers, actin7F, actin7R, X5-GSTF and X5-GSTR were added. Finally, 2 μl of 1 μg/μl RNA sample was added. The totally volume of the PCR reaction was 50 μl. The first cDNA strand synthesis was carried out at 42° C. for 30 minutes. Then the tube was heated to 95° C. to inactivate the MMLV RT, then the normal PCR was started. The PCR condition were: 25 cycles of 95° C. for 1 min, 55° C. for 1 min and 72° C. for 1 min. The sequence of the actin7F prime was 5'-GGT GAG GAT ATT CAG CCA CTT GTC TG-3' (SEQ ID NO: 14), and that of the actin7R was 5'-TGT GAG ATC CCG ACC CGC AAG ATC-3' (SEQ ID NO: 15).

For detecting the RT-PCR product by mini-southern blot, the PCR product was equally loaded in two agars gel wells and transferred to hybond-N⁺ membrane by using 0.4 M NaOH overnight at room temperature.

For hybridization, one set of the membrane was probed with α-$^{32}$P labeled actin 7 probe and the other set was probed with α-$^{32}$P labeled AtNHX5 specific probe. The RTPCR reactions were repeated several times, and all the results were subjected to statistical analysis.

Results

Cloning AtNHX5 cDNA

Through the screening of an *Arabidopsis* cDNA library, only partial sequence of AtNHX5 was obtained, which coded for 350 amino acids. According to this partial sequence, an AtNHX5 specific 3'-primer, X5 REV was designed for 5'-RACE to obtain the 5'-end, and then an AtNHX5 specific 5'-primer, X5-5'-RACE, was designed for 3'-RACE to obtain the full length of AtNHX5. The open reading frame of AtNHX5 was a 1563-bp fragment (SEQ ID NO:4) which coded for 521 amino acids (SEQ ID NO:5) (FIG. 1). One amiloride binding site (FFLFLLPPII (SEQ ID NO: 16)) was located in the N-terminus of AtNHX5. The topology prediction (using TopPred 2) showed that the full length AtNHX5 protein has 11 transmembrane domains.

The Natural Subcellular Distribution of AtNHX5

Figure 2:
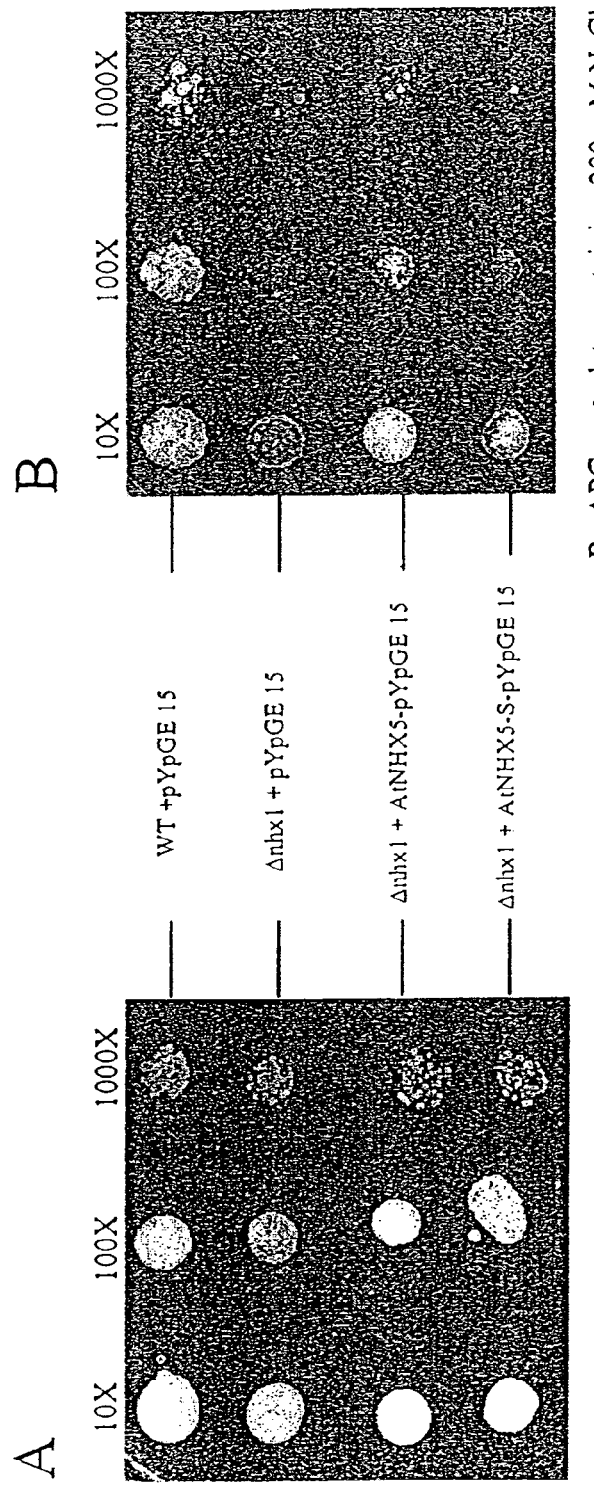
FIG. 2 shows the salt tolerance test of different yeast transformants. On both A and B plates, equal amount of yeasts cells of different transformants were loaded at 10×, 100× and 1000× dilutions.

In order to detect the subcellular location of AtNHX5, wild type *Arabidopsis* cellular membrane fractions, including tonoplast, mitochondria, plasma membrane, and ER, were prepared using sucrose gradient sedimentation, and 40 µg of each kind of membrane proteins was subjected to Western-blotting by using antibody against AtNHX5. The result shows a strong band around 45 KDa exclusively located on tonoplast (FIG. 2, lane1). The molecular weight of the band was smaller than expected, which was 56 Kda. This could be due to specific cleavage or modification of protein by the plant, or protein degradation, or abnormal migration caused by the interference of lipid component from the membrane.

The Expression Pattern of AtNHX5 and its Response to Salt Treatment

30 µg of each kind of RNA sample was subjected to a formaldehyde denatured agarose gel electrophoresis and then transferred to Hybond-N+ membrane. The membrane was probed with $\alpha$-$^{32}$P labeled AtNHX5 cDNA. Phosphoreimage results showed a weak band around 2.1 kb in leaf, stem and root tissues, but not in the flower tissue, and there was no band in the salt-treated leaf tissue either. In order to confirm the Northern-blotting result, semi-quantitative RT-PCR was performed. Actin-7 was used as an internal control. The expected size of actin7 band was 550 bp, and that of AtNHX5 was 315 bp. The semi-quantitative RT-PCR results suggested that AtNHX5 was expressed in a slightly lower level in flower than in the other tissues, but the difference was not statistically significant.

To detect the expression of AtNHX5 indifferent developmental stages, RNA sample from 1-month old seedlings grown on MS-agar plates was prepared and subjected to semi-quantitative RT-PCR, and the results were compared with those results gotten from adult plant. No statistically significant difference between the seedling sample and the adult samples at the AtNHX5 mRNA level was detected.

These results suggest that AtNHX5 might be expressed constantly from young seedling to adult stage, and it does not response to salt treatment significantly.

The Function of AtNHX5

The function of AtNHX5 was tested by both yeast complementation and overexpression in Arabidopsis.

Yeast Complementation

For yeast complementation experiment, the ORF of AtNHX5 was cloned into a yeast expression vector, pYpGE 15, under PGK promoter, and the resulting construct (AtNHX5-pYpGE15) and the empty pYpGE15 vector were used respectively to transform a yeast salt sensitive mutant, Δnhx1, by Lithium actetate method (material and method). As a control, wild type yeast strain was also transformed with empty pYpGE15 vector. The salt tolerance of the different transformants was tested by plating equal amount of yeast cells of each kind on APG plates containing 200 mM NaCl under pH5.5. The result showed that the growth of Δnhx1 with empty pYpGE15 vector was inhibited by 200 mM NaCl, but AtNHX5 could suppress the salt sensitivity of the Δnhx1 mutant strain (FIG. 2).

In order to check the effect of C-terminus of AtNHX5, a short version of AtNHX5 ORF (called AtNHX5-S) which codes the first 350 amino acids was also used to do the yeast complementation experiment, and the result showed that AtNHX5-S could complement the mutated ScNHX1 function, but not as well as the full ORF of AtNHX5 did. This result suggests that the C-terminus of AtNHX5 might have a regulatory function (FIG. 2).

Western-blotting was used to detect the expression in yeast of both the full and short length of AtNHX5. Tonoplast samples from transformants with full ORF and with short ORF of AtNHX5, as well as from Δnhx1 with empty pYpGE15 strain were prepared, and 60 µg of each sample was used to do Western blot. The results show a 57 KDa band for the full ORF transformants (FIG. 2A), and a 40 KDa band for the short ORF transformants (FIG. 2B). Both of these two bands had the expected sizes.

Based on the results described above, AtNHX5 may have the same function as ScNHX1.

AtNHX5 Transgenic *Arabidopsis* Plants

The ORF of AtNHX5 was cloned into a plant expression vector (pBISN1) under the supermas promoter, with Kanamycin selection marker, at 5' SalI site and 3' SmaI site. And *Agrobacterium* mediated transformation protocol was used to obtain transgenic plants.

To transgenic seeds were first screened on MS-K25-agar plates. Totally 15 lines survived. Then T$_1$ seeds of two lines (AtNHX5-L1 and AtNHX5-L2) were plated on MS-K25-agar plates containing 50, 100, 150, and 200 mM NaCl. There were several seedlings from each of the two lines, which survived on 50 and 100 mM NaCl plates, but not on the 150 mM NaCl and above plates. Then the surviving seedlings from the 100 mM NaCl MS-K25-agar plates were transferred to soil. Ten days after the transfer, a set of three plants of each line were started to be watered with 0, 100, and 200 mM NaCl solutions every other day. Meantime, as controls, a set of wild type plants were also treated the same way. After watered with 200 mM NaCl for 2 weeks, the wild type plant was almost dead completely, while one transgenic line, AtNHX5-L2, was still as green as its control plant which was watered with 0 mM NaCl.

The mRNA level of AtNHX5 in both AtNHX5-L2 line and wild type were tested. RNA samples from young seedlings of AtNHX5-L2 line and wild type (from MS plates) were prepared and subjected to semi-quantitative RT-PCR. The same AtNHX5 specific primers and actin7 control primers used for detecting the tissue distribution of AtNHX5 were used here. The results showed that AtNHX5 mRNA was about 4 times higher in AtNHX5-L2 line than in wild type. Therefore, overexpression of AtNHX5 in *Arabidopsis* can confer a higher salt tolerance to the plants.

EXAMPLE 13

Cloning and Characterization of NX4

PCR primers were designed for the amplification of the AtNHX2 sequence based on a BAC DNA sequence (T9J14.2) with a predicted amino acid sequence that showed homology to AtNHX1:

```
X2F,
5'-TTCGCCTCTTTAACCTCTAAAATG-3'    (SEQ ID NO: 17)

X2R,
5'-TGTAGGCAAGAGCCATAGATACAG-3'    (SEQ ID NO: 18)
```

A single band of approximately 1.2 kb was amplified from a size fractionated flower cDNA library (CD4-6, ABRC) and was used as a template for screening the flower cDNA library with $^{32}$P-labeled probes. Plaques hybridizing to the probe in the first round were subjected to a second round using the same probe. The largest clone obtained from excised phagemids from the second round of screening was incomplete at the N-terminus coding portion of the gene. The 5' end of the cDNA was first determined using 5'-rapid amplification of cDNA ends (RACE). A 5'-RACE primer, which primes transcription towards the 5'-end of the cDNA, was designed for use with the SMART RACE cDNA amplification kit (Clontech):

X2-5'RACE1, 5'-TACAGAGTCGGTTGCAG-CAAATATGGCG-3' (SEQ ID NO: 19)

5'-RACE was performed with 3 µg of RNA isolated from flower tissues of *A. thaliana* (Col) according to manufacturer's instructions. A single-800 bp fragment was amplified, cloned into Invitrogen pCR2.1 TOPO vector using the Invitrogen TOPO TA Cloning Kit according to the manufacturer's instructions. Using the most extreme 5'-sequence from the 5'-RACE and the most extreme 3'-sequence from the original screen, two primers were designed for amplification of the full-length cDNA:

```
X2-3'END,
5'-CACCAATACTAGTCACCATAAGAGGGAAGAGCA-3';   (SEQ ID NO: 20)

X2-5'END,
5'-CTGCCTCTCTCTCAACGCAACTCAATCCA-3'        (SEQ ID NO: 21)
```

Using these primers and the RACE-ready cDNA prepared from RNA isolated from flower tissues of *A. thaliana* (Col), a 2.1 kb product was amplified according to manufacturer's instructions. This was submitted for complete sequencing and compared with sequences obtained from the original library clone and RACE product. SEQ ID NO:1 and SEQ ID NO:2 list the full length nucleotide sequence and the derived protein sequence, respectively.

EXAMPLE 14

Cloning and Characterization of NX4

PCR primers were designed for the amplification of the AtNHX2 sequence based on a BAC DNA sequence (F24P17.16) with a predicted amino acid sequence that showed homology to AtNHX1. The cloning and sequencing of AtNHX5 was undertaken by Dr. Xue-Jun Hua. The full-length AtNHX4 cDNA was isolated from the Δ-PRL-2 Arabidopsis cDNA library (ABRC).

RT-PCR

RT-PCR-was carried out using the Ready-to-Go PCR and RT-PCR beads (Amersham Pharmacia Biotech, Piscataway, N.J.) according to the manufacturer's conditions. Reactions were carried out on a 50 µl volume containing 45 µl DEPC-H$_2$O, 1 µl Oligo dT (0.5 µg/µl) and 0.5 µl of each of the primers described below (In situ methods) and 2 µg RNA. The same primer pairs were used for the RT-PCR as for the amplification of gene-specific probes described below (see FIG. 2). Where RT-PCR products were not detectable with ethidium bromide staining of the agarose gel, DNA blots of the RT-PCR reactions were probed with $^{32}$P-labeled probes. These probes were made using the amplification products from the primers above and the cDNAs of each gene.

In Situ Hybridization

Unique regions of each cDNA were selected for amplification of probe templates so that we could be certain that signals, when detected for the in situ hybridization as with the RT-PCR above, were specific for the particular gene of interest. The following primer pairs, given here as gene name, region of the cDNA from which it was amplified, amplicon size, and then primer pair, were used to amplify PCR products for cloning into the pSPT18 and pSPT19 cloning vectors (Roche, Indianapolis, Ind.):

AtNHX2, 5'-UTR, 353 bp

```
X2ECO
5'-GAATTCCTCAACGCAACTCAATCCAC-3'    (SEQ ID NO: 22)

X2PST
5'-CTGCAGGGCGAACATTGTCATCTTTC-3'    (SEQ ID NO: 23)
```

AtNHX4, 3'-UTR, 474 bp

```
X4ECO
5'-GAATTCCATTGAGAATAGTGTTCCGCAA-3'  (SEQ ID NO: 24)

X4PST
5'-CTGCAGGATTCGTGTCCCTTTGTTTTG-3'   (SEQ ID NO: 25)
```

AtNHX5, central portion of ORF, 502 bp

```
X5ECO
5'-GAATTCTCGCTTCAGTTGTTACTGGTG-3'   (SEQ ID NO: 26)

X5PST
5'-CTGCAGCGCTTCATAACAATTCCTGTCA-3'  (SEQ ID NO: 27)
```

DIG-labeled sense and antisense probes were synthesized and labeling efficiency was evaluated according to manufacturer's instructions (DIG RNA Labeling Kit, Roche, Indianapolis, Ind.).

In situ hybridization was performed as described by Long et al. (1996), except for the following modifications. *Arabidopsis thaliana* ecotype Columbia plant tissues were fixed in 4% paraformaldehyde and dehydrated through an ethanol and ter-butyl alcohol series before embedding in paraffin. Seven-µm-thick sections were adhered to ProbeOn Plus slides (Fisher, Pittsburgh, Pa.), deparaffinized with Histoclear, rehydrated through an ethanol series, treated for 30 min with 1 µg/mL proteinase K, refixed with paraformaldehyde, treated with 0.1 M acetic anhydride, and dehydrated through an ethanol series. Slide pairs were incubated with equal concentrations of sense and antisense probes at 55° C. overnight. Post-hybridization treatment, including washes and RNAse treatment, was also as described by Long et al. (1996). Alkaline-phosphatase conjugated anti-DIG antibodies were used to detect DIG-labeled probes. NBT/BCIP (Invitrogen, Carlsbad, Calif.) was incubated with the slides to generate a color reaction with the alkaline phosphatase bound to the antibody. Slides were dehydrated and mounted with Permount (Sigma, St. Louis, Mo.).

In situ hybridizations for detection of AtNHX2 and AtNHX4 echo the results of the RT-PCR. AtNHX2 shows specific floral expression particularly in the septum of the carpel. Signals for antisense probes of AtNHX2 were not detected in other tissues. AtNHX4 signal was observed only in roots. AtNHX2, although detectable in tapetal cells, is most strongly expressed in the septum of the developing silique. AtNHX4 showed a very tissue-specific expression, both by RT-PCR and in situ analyses. Signal for AtNHX4 expression was detectable only in roots; however, no cell-specific conclusions can be made regarding AtNHX4 expression because of the poor preservation of root sections in the in situ protocol.

The present invention has been described in detail and with particular reference to the preferred embodiments;

however, it will be understood by one having ordinary skill in the art that changes can be made thereto without departing from the spirit and scope of the invention.

All articles, patents and other documents described in this application (including Genbank sequences and/or accession numbers), U.S. application No. 60/078,474 (filed Mar. 18, 1998), U.S. application No. 60/116,111 (filed Jan. 15, 1998) and U.S. Pat. Nos. 5,612,191, 5,763,211, 5,750,848 and 5,681,714, are incorporated by reference in their entirety to the same extent as if each individual publication, patent or document was specifically and individually indicated to be incorporated by reference in its entirety. They are also incorporated to the extent that they supplement, explain, provide a background for, or teach methodology, techniques and/or compositions employed herein.

The following is a non-limiting list of plants which find use in the present invention: Alfalfa, Almond, Apple, Apricot, Arabidopsis, Artichoke, Atriplex, Avocado, Barley, Beet, Birch, Brassica, Cabbage, Cacao, Cantaloup/cantalope, Carnations, Castorbean, Cauliflower, Celery, Clover, Coffee, Corn, Cotton, Cucumber, Garlic, Grape, Grapefruit, Hemp, Hops, Lettuce, Maple, Melon, Mustard, Oak, Oat, Olive, Onion, Orange, Pea, Peach, Pear, Pepper, Pine, Plum, Poplar, Potato, Prune, Radish, Rape, Rice, Roses, Rye, Sorghum, Soybean, Spinach, Squash, Strawberries, Sunflower, Sweet corn, Tobacco, Tomato and Wheat.

TABLE 4

| Hybridization | Wash |
|---|---|
| High Stringency (very similar sequences) | |
| 55-65° C. | 60-65° C. |
| 5×SSC | 0.1×SSC |
| 2% SDS | 0.1% SDS |
| 100 ug/ml SSDNA | |
| High to Moderate Stringency (similar sequences) | |
| 40-50° C. | 50° C. |
| 5×SSC | 0.1×SSC |
| 2% SDS | 0.1% SDS |
| 100 ug/ml SSDNA | |
| Low Stringency (low similarity among sequences) | |
| 30-40° C. | 40-50° C. |
| 5×SSC | 2×SSC |
| 2% SDS | 0.2% SDS |
| 100 ug/ml SSDNA | |

Abbreviations:
SSC = sodium chloride-sodium citrate buffer
SSDNA = single stranded DNA

REFERENCES (1) Rush, P W and Epstein, E (1981). J. Amer. Soc. Hort. Sci. 106, 699-704.
(2) Norlyn, J D (1980). In: Genetic Engineering of Osmoregulation (Eds. D W Rains, R C Valentine and A Hollaender) pp. 293-309. Plenum Press: New York.
(3) Tal, M (1985). Plant & Soil 89, 199-226.
(4) Flowers, T J and Yeo, A R (1995). Aust. J. Plant Physiol. 22, 875-884.
(5) Bonhert, H J and Jensen, R G (1996). Aust J. Plant Physiol. 23, 661-667.
(6) Tarcynski, M C, Jensen, R G & Bonhert, H J. (1995) Science 259, 508-510.
(7) Kishor et al. (1995). Plant Physiol. 108, 1387-1394.
(8) Ishitani, M, et al., (1995). Plant Mol. Biol. 27, 307-317
(91 Xu, et al. (1996) Plant Physiol. 110, 249-257.
(10) Wu, R and Ho, THD. Patent #W09713843.
(11) Jia, Z, et al., (1992). EMBO J. 11, 1631-1640.
(121 Young, P G & Zheng, P. J. Patent #W09106651.
(13) Blumwald, E & Poole, R. J. (1985) Plant Physiol. 78, 163-167.
(14) Blumwald, E et al., (1987). Plant Physiol. 85, 30-33.
(15) Blumwald, E & Poole, R. J. (1987) Plant Physiol. 83, 884-887.
(16) Barkla, B J, et al., (1990). Plant Physiol. 93, 924-930.
(17) Barkla, B. J. & Blumwald, E. (1991) Proc. Natl. Acad. Sci. USA 88, 11777-11181.
(18) Blumwald, E. & Gelli, A. (1997). Adv. Bot. Res. 25, 401-417.
(19) Thompson, J D et al., Nucleic Acid Res. 22:4673-4680.
(20) Ni et al., (1995) Plant Journal 7:661-676
(21) Shah et al., (1986) Science 233:478-481.
(22) Ono et al., (1996) Plant Physiol 112:483-491
(23) Abe et al., (1997) Plant Cell 9:1859-1868.
(24) Rieping M and Schoffl F (1992) Mol Gen Genet 231:226-232).
(25) Raghothama et al., (1997) Plant Mol Biol 34:393-402).
(26) Mett et al., (1996) Transgenic Res 5:105-113.
(27) Schena et al., (1991) PNAS 88:10421-10425.
(28) Vorst et al. (1990) Plant Mol Biol 14:491-499.
(29) Wanapu & Shinmyo (1996) Ann. NY Acad. Sci. 782: 107-114.
(30) Harlow E & Lane D (1988). Antibodies: a laboratory manual. Cold Spring Harbor Laboratory Press. New York.
(31) Sambrook, J, Fritsch, E. E. & Maniatis, T. (1989). Molecular Cloning: A laboratory manual. Cold Spring Harbor Laboratory Press. New York.
(32) Lee, C. C. & Caskey, T. in: PCR Protocols: A guide to Methods and Applications. Academic Press, Inc. San Diego. pp. 46-53
(33) Narasimhulu, S B, et al., Plant Cell 8:873-886 (1996))
(34) McCormac A C. et al., (1997) Mol Biotechnol. 8:199-213.
(35) Ma H, et al., (1987) Gene 58:202-226
(36) Gietz R D & Woods, R A (1994). High efficiency transformation with lithium acetate. In Molecular Genetics of Yeast, A Practical Approach (J. Johnston, ed.) New York: IRL Press. pp. 121-134.
(37) Gietz, R D & Sugino, A (1988), Gene 74: 527-534.
(38) Krieber et al. (1993) Cell 72:427-441.
(i) Blumwald, E. (1987). Physiol. Plant 69, 731-734.
(ii) Blumwald, E. & Poole, R. J. (1986). Plant Physiol. 80, 727-731.
(iii) Clough, M. & Bent, A. (1997). Arabidopsis Meeting, Madison, Wis.,
(iv) Moloney, M. M., Walker, J. M., & Sharma, K. K. (1989). Plant Cell Rep. 8, 238-242.
(v) Tomes, D. T., Ross, M. C., & Songstad, D. D. (1995). In:Plant Cell, Tissue and Organ Culture (O. L. Gamborg & G. C. Phillips, eds). Springer, New York. pp 197-213.
(vi) Amstrong, C. L., & Green, C. E. (1985). Planta 164, 207-214.

We claim:

1. An isolated nucleic acid molecule comprising the nucleotide sequence of SEQ ID NO: 1 or a nucleic acid that encodes SEQ ID NO: 2.

2. A vector comprising the nucleic acid molecule of claim 1.

3. The vector of claim 2 comprising a promoter, wherein the promoter is operatively linked to the nucleic acid molecule, wherein the promoter is selected from the group consisting of a super promoter, a 35S promoter of cauliflower mosaic virus, a drought-inducible promoter, an ABA-inducible promoter, a heat shock-inducible promoter, a salt-inducible promoter, a copper-inducible promoter, a steroid-inducible promoter and a tissue-specific promoter.

4. A host cell comprising the vector of claim 2.

5. The host cell of claim 4, wherein said host cell is selected from the group consisting of a fungal cell, a yeast cell, a bacterial cell and a plant cell.

6. A transgenic plant, a plant part, a seed, a plant cell or progeny thereof, wherein the plant, plant seed, plant cell or progeny comprises a construct comprising the nucleic acid molecule of claim 1.

7. The plant part of claim 6, comprising all or part of a leaf, a flower, a stem, a root or a tuber.

8. The plant, plant part, seed, plant cell or progeny of claim 6, wherein the plant, plant part, seed, plant cell or progeny is of a species selected from the group consisting of potato, tomato, *Brassica*, cotton, sunflower, strawberry, spinach, lettuce, rice, soybean, corn, wheat, rye, barley, atriplex, sorghum, alfalfa, *Salicornia*, almond, apple, apricot, *Arabidopsis*, artichoke, avocado, beet, birch, cabbage, cacao, cantaloupe/cantaloup, carnation, castorbean, cauliflower, celery, clover, coffee, cucumber, garlic, grape, grapefruit, hemp, hops, maple, melon, mustard, oak, oat, olive, onion, orange, pea, peach, pear, peanut, pepper, pine, plum, poplar, prune, radish, rape, rose, squash, sweet corn, and tobacco.

9. The plant, plant part, seed, plant cell or progeny of claim 6, wherein the plant is a dicot plant.

10. The plant, plant part, seed, plant cell or progeny of claim 6, wherein the plant is a monocot plant.

11. A transgenic plant comprising recombinant DNA, wherein the recombinant DNA encodes a polypeptide comprising the polypeptide sequence of SEQ ID NO:2.

12. A transgenic plant comprising a recombinant nucleic acid molecule, wherein said nucleic acid molecule comprises SEQ ID NO: 1 or a nucleic acid encoding SEQ ID NO: 2 and a promoter.

13. The transgenic plant of claim 12, wherein the recombinant nucleic acid molecule is operatively linked to a constitutive promoter sequence or an inducible promoter sequence, that provides transcription of the recombinant nucleic acid molecule in the plant.

14. The transgenic plant of claim 12, wherein the recombinant nucleic acid molecule is chemically synthesized.

15. The transgenic plant of claim 12, wherein the recombinant nucleic acid molecule is isolated from *Arabidopsis thaliana*.

16. An expression transgene comprising a recombinant nucleic acid molecule operably linked to a promoter selected from the group consisting of a super promoter, a 35S promoter of cauliflower mosaic virus, a drought-inducible promoter, an ABA-inducible promoter, a heat shock-inducible promoter, a salt-inducible promoter, a copper-inducible promoter, a steroid-inducible promoter and a tissue-specific promoter, wherein said nucleic acid molecule comprises SEQ ID NO: 1 or a nucleic acid encoding SEQ ID NO: 2.

17. A plant, a plant part, a seed, a plant cell or progeny thereof, comprising the expression transgene of claim 16.

18. The plant part of claim 17, comprising all or part of a leaf, a flower, a stem, a root or a tuber.

19. The plant, plant part, seed, plant cell or progeny of claim 17, wherein the plant, plant part, seed, plant cell or progeny is of a species selected from the group consisting of potato, tomato, *Brassica*, cotton, sunflower, strawberry, spinach, lettuce, rice, soybean, corn, wheat, rye, barley, atriplex, sorghum, alfalfa, *Salicornia*, almond, apple, apricot, *Arabidopsis*, artichoke, avocado, beet, birch, cabbage, cacao, cantaloupe/cantaloup, carnation, castorbean, cauliflower, celery, clover, coffee, cucumber, garlic, grape, grapefruit, hemp, hops, maple, melon, mustard, oak, oat, olive, onion, orange, pea, peach, pear, peanut, pepper, pine, plum, poplar, prune, radish, rape, rose, squash, sweet corn, and tobacco.

20. The plant, plant part, seed, plant cell or progeny of claim 17, wherein the plant is a dicot plant.

21. The plant, plant part, seed, plant cell or progeny of claim 17, wherein the plant is a monocot plant.

22. A method for producing a recombinant plant cell that expresses a nucleic acid molecule, wherein the method comprises introducing into a plant cell the expression transgene of claim 16.

23. A method of producing a genetically transformed plant, wherein the method comprises regenerating a genetically transformed plant from the plant cell, seed, plant part or progeny thereof of claim 17.

24. A transgenic plant produced according to the method of claim 23.

25. A method for expressing a polypeptide in a plant cell or progeny thereof, wherein the method comprises culturing the plant cell or progeny of claim 17 under conditions suitable for gene expression.

26. A method for producing a transgenic plant comprising transforming a plant with the expression transgene of claim 16.

27. A method of producing a genetically transformed plant, wherein the method comprises:
   (a) cloning or synthesizing a nucleic acid molecule comprising
      SEQ ID NO: 1 or
      a nucleic acid encoding SEQ ID NO: 2;
   (b) inserting the nucleic acid molecule into a vector so that the nucleic acid molecule is operably linked to a promoter;
   (c) inserting the vector into a plant cell or plant seed; and
   (d) regenerating a plant from the plant cell or plant seed.

28. A transgenic plant produced according to the method of claim 27.

29. The transgenic plant of claim 12, wherein the recombinant nucleic acid molecule comprises a nucleic acid encoding SEQ ID NO:2.

30. The expression transgene of claim 16, wherein the recombinant nucleic acid molecule comprises a nucleic acid encoding SEQ ID NO:2.

31. The method of claim 27, wherein the nucleic acid molecule in step (b) comprises a nucleic acid encoding SEQ ID NO:2.

* * * * *